United States Patent [19]
Zamora et al.

[11] Patent Number: 5,985,240
[45] Date of Patent: Nov. 16, 1999

[54] PEPTIDE RADIOPHARMACEUTICAL APPLICATIONS

[75] Inventors: Paul O. Zamora, Guadalajara, Mexico; Buck A. Rhodes; Michael J. Marek, both of Albuquerque, N.Mex.

[73] Assignee: RhoMed Incorporated, Princeton, N.J.

[21] Appl. No.: 08/651,179

[22] Filed: May 21, 1996

Related U.S. Application Data

[63] Continuation-in-part of application No. 08/447,453, May 23, 1995, which is a continuation-in-part of application No. 08/269,929, Jun. 30, 1994, Pat. No. 5,759,515, which is a continuation-in-part of application No. 08/087,219, Jul. 2, 1993, Pat. No. 5,700,444, which is a continuation-in-part of application No. 07/840,077, Feb. 20, 1992, Pat. No. 5,443,816, which is a continuation-in-part of application No. 07/565,275, Aug. 8, 1990, Pat. No. 5,102,990, which is a continuation-in-part of application No. 07/391,474, Aug. 9, 1989, Pat. No. 5,078,985

[60] Provisional application No. 60/011,027, Feb. 2, 1996.

[51] Int. Cl.⁶ .......................... A61K 51/00; A61M 36/14
[52] U.S. Cl. ..................... 424/1.69; 424/1.11; 424/1.65; 530/311
[58] Field of Search .................. 424/1.11, 1.37, 424/1.65, 1.69, 9.1, 400; 530/300, 311, 324–330, 333, 334, 317, 338; 534/7, 10–16; 206/223, 569, 570

[56] References Cited

U.S. PATENT DOCUMENTS

| | | | |
|---|---|---|---|
| 4,424,200 | 1/1984 | Crockford et al. | 424/1.1 |
| 4,427,646 | 1/1984 | Olexa et al. | 424/1.1 |
| 4,479,930 | 10/1984 | Hnatowich | 424/1.1 |
| 4,612,302 | 9/1986 | Szabo et al. | 514/11 |
| 4,668,503 | 5/1987 | Hnatowich | 424/1.1 |
| 4,732,864 | 3/1988 | Tolman | 436/547 |
| 4,904,642 | 2/1990 | Coy et al. | 514/11 |
| 4,986,979 | 1/1991 | Morgan, Jr. et al. | 424/1.1 |
| 5,011,676 | 4/1991 | Thakur | 424/1.1 |
| 5,021,235 | 6/1991 | Pipes | 424/1.1 |
| 5,039,662 | 8/1991 | Schasteen | 514/17 |
| 5,051,641 | 9/1991 | Shochat et al. | 436/545 |
| 5,078,985 | 1/1992 | Rhodes | 424/1.11 |
| 5,091,514 | 2/1992 | Fritzberg et al. | 534/14 |
| 5,092,885 | 3/1992 | Yamada et al. | 623/11 |
| 5,102,990 | 4/1992 | Rhodes | 530/391.5 |
| 5,128,119 | 7/1992 | Griffiths | 424/1.1 |
| 5,162,505 | 11/1992 | Dean et al. | 530/391.5 |
| 5,169,933 | 12/1992 | Anderson et al. | 530/391.3 |
| 5,225,180 | 7/1993 | Dean et al. | 424/1.1 |
| 5,225,530 | 7/1993 | Bernardi et al. | 530/324 |
| 5,229,490 | 7/1993 | Tam | 530/324 |
| 5,236,903 | 8/1993 | Saiki et al. | 514/12 |
| 5,308,603 | 5/1994 | Thakur | 424/1.49 |
| 5,328,679 | 7/1994 | Hansen et al. | 424/1.49 |
| 5,371,184 | 12/1994 | Rajagopalan et al. | 530/324 |
| 5,376,356 | 12/1994 | Morgan, Jr. | 424/141 |
| 5,382,654 | 1/1995 | Lyle et al. | 530/311 |
| 5,384,113 | 1/1995 | Deutsch et al. | 424/1.69 |
| 5,405,597 | 4/1995 | Dean et al. | 424/1.69 |
| 5,443,815 | 8/1995 | Dean et al. | 424/141 |
| 5,443,816 | 8/1995 | Zamora et al. | 424/1.69 |
| 5,460,785 | 10/1995 | Rhodes et al. | 424/1.49 |
| 5,620,675 | 4/1997 | McBride et al. | 424/1.69 |
| 5,632,969 | 5/1997 | Flanagan et al. | 424/1.69 |
| 5,679,318 | 10/1997 | Vanderheyden et al. | 424/1.11 |

FOREIGN PATENT DOCUMENTS

| | | | |
|---|---|---|---|
| 2016235 | 11/1990 | Canada | 530/7.06 |
| 0196669 | 4/1986 | European Pat. Off. | C07K 17/06 |
| 0 237 150 A2 | 1/1987 | European Pat. Off. | A61K 49/02 |
| 0250013 | 5/1987 | European Pat. Off. | C07F 13/00 |
| 0 284 071 A2 | 9/1988 | European Pat. Off. | C07K 15/00 |
| 89114365 | 4/1990 | European Pat. Off. | C07K 7/26 |
| 92810381 | 11/1992 | European Pat. Off. | C07K 7/26 |
| 94810008 | 7/1994 | European Pat. Off. | C07K 7/26 |
| 2225579A | 6/1990 | United Kingdom | C07K 7/26 |
| WO 90/15818 | 6/1989 | WIPO | C07K 5/08 |
| WO 92/13572 | 2/1992 | WIPO | A61K 49/02 |
| PCT/US93/06029 | 1/1994 | WIPO | C07K 7/26 |
| WO 95/11045 | 10/1994 | WIPO | A61K 51/08 |
| PCT/US94/06274 | 1/1995 | WIPO | C07K 14/655 |
| PCT/US94/08335 | 2/1995 | WIPO | C07K 14/655 |

OTHER PUBLICATIONS

Fischman, A.J., et al., "A Ticket to Ride: Peptide Radiopharmaceuticals," *J Nucl Med*, vol. 34, No. 12, pp. 2253–2263 (1993).

Hynes, R.O., "Inegrins: Versatility, Modulation, and Signaling in Cell Adhesion," *Cell*, vol. 69, pp. 11–25 (1992).

Ill, C.R., et al., "Adhesion of Platelets to Laminin in the Absence of Activation," *J Cell Bio*, vol. 99, pp. 2140–2145, (1984).

Khaw, B.A., et al., "Technetium–99m Labeling of Antibodies to Cardiac Myosin Fab and to Human Fibrinogen," *J Nucl Med*, vol. 23, No. 11, pp. 1011–1019 (1982).

(List continued on next page.)

Primary Examiner—Jose' G. Dees
Assistant Examiner—Dameron Jones
Attorney, Agent, or Firm—Darby & Darby

[57] ABSTRACT

The invention relates to radiotherapy with somatostatin-derived peptides labeled with medically useful metal ions. The invention in particular provides for methods and reagents for labeling somatostatin-derived peptides with perrhenate, in which a solution including somatostatin-derived peptide analogue containing at least one disulfide bond is provided, the solution is reacted with stannous ions and with a radioisotope, wherein the stannous ions are sufficient to substantially reduce the disulfide bonds of the peptide and the radioisotope, and the radiolabeled somatostatin-derived peptide analogue recovered. Also provided are methods for regional administration of radiolabeled somatostatin-derived peptides, methods for enhanced regional retention of radiolabeled somatostatin-derived peptides, methods for treatment of arthritis using radiolabeled somatostatin derived peptides, and methods for stabilizing radiolabeled somatostatin derived peptides.

5 Claims, 8 Drawing Sheets

OTHER PUBLICATIONS

Knight, L.C., et al., "Thrombus Imaging with TC–99m Synthetic Peptides Reactive with Activated Platelets," *J Nucl Med*, vol. 31, No. 5, No. 209 Abstract (May 1990).

Kondo, M., et al., "Studies of Dimeric IMLF with High Chemotactic Activities," *Peptides: Chemistry and Biology*, JA Smith and JE Rivier, eds., ESCOM, Leiden, pp. 425–426 (1992).

Krenning EP, Kwekkeboom DJ, Bakker WH, Breeman WA, Kooij PP, et al: Somatostatin receptor scintigraphy with [111In–DTPA–D–Phe1]– and [1231–Tyr3]–octreotide; the Rotterdam experience with more than 1000 patients. *Eur J Nucl Med* 20: 716–731, 1993.

Kraus, J, et al., "Cyclic Tetrameric Clusters of Chemotactic Peptides as Superactive Activators of Lysozyme Release from Human Meutrophils," *Bilchem and Biophy Res Comm*, vol. 124, No. 3, pp. 939–944 (1984).

Sonnenberg, A., et al., "Isolation of $\partial 6\beta 1$ Integrins from Platelets and Adherent Cells by Chromatography on Mouse Laminin Fragment E8 and Human Laminin Pepsin Fragment," *Exp Cell Res*, vol. 197, pp. 234–244 (1991).

Tandon, N.N. et al., "Interaction of Human Platelets with Laminin and Identification of 67 kDa Laminin Receptor on Platelets," *Riochem J*, vol. 2724, pp. 535–542 (1991).

Swanson, D., et al., "In–111 Laminin Peptide Fragments for Malignant Tumor Detection," *J Nucl Med*, 34, 231P Abstract (1993).

Wraight, E.P., et al., "The Use of Chelating Derivative of Alpha Melanocyte Stimulating Hormone for the Clinical Imaging of Malignant Melanoma," *Brit J Rad*, vol. 65, pp. 112–118 (1992).

Yamada, K.M., "Adhesive Recognition Sequences," *J Biol Chem*, vol. 266, No. 20, pp. 12809–12812 (1992).

Akers MJ, "Antioxidants in Pharmaceutical Products", *J. of Paren. Sci. & Tech.* 36: 222–228 (1982).

Ballinger J, et al., "Stabilization of 99mTc–Pyrophosphate Injection with Gentisic Acid", *Eur. J. Nuc. Med.* 6:153–154 (1981).

Bender H, et al, "Local and Regional Therapy of Tumors With 188Re–RC–160: Clinical Aspects", appearing in *Radionuclides for Receptors*, 1995 (published after filing date of parent application).

Cai RZ, et al., "Synthesis and biological activity of highly potent octapeptide analogs of somatostatin", *Proc. Natl. Acad. Sci. USA*, 83: 1896–1900 (1986).

Chinol M, et al., "Chemistry and Biological Behavior of Samarium–153 and Rhenium–186–Labeled Hydroxyapatite Particles: Potential Radiopharmaceuticals for Radiation Synovectomy", *J. Nuc. Med.*, 34: 1536–1542 (1993).

Deutsch E, et al., "Radiation synovectomy revisited", *Eur. J. Nuc. Med.* 20:1113–1127 (1993).

Fioravanti A, et al., "Valutazione dell' efficacia della somatostatina per via intraarticolare in pazienti con artrite reumatoide", *La Clin. Ter.* 142: 453–457 (1993) (English abstract provided).

Matucci–Cerinic M, et al., "Gold Salts and Somatostatin: A New Combined Analgesic Treatment For Psoriatic Arthritis", *Drugs Exp. Clin. Res.* 18: 53–61 (1992).

Tofe AJ, et al., "In Vitro Stabilization of a Low–Tin Bone––Imaging Agent (99mTc—Sn–HEDP) by Ascorbic Acid", *J. of Nuc. Med.* 17: 820–825 (1976).

Tofe AJ, et al., "Gentisic Acid: A New Stabilizer for Low Tin Skeletal Imaging Agents: Concise Communication", *J. of Nuc. Med.* 21: 366–370 (1979).

Will R, et al., "Comparison of two yttrium–90 regimens in inflammatory and osteoarthropathies", *Ann. Rheum. Dis.* 51: 262–265 (1993).

Zamora PO, et al., "Experimental Radiotherapy of Receptor–Positive Human Prostate Adenocarcinoma With 188Re–RC–160, A Directly–Radiolabeled Somatostatin Analogue", *Int. J. Cancer* 65: 214–220 (1996).

Bard, D.R., et al., "BisMSH–DTPA: A Potential Imaging Agent for Malignant Melanoma," *Ann NY Acad Sci.* 680, pp. 451–453 (1993).

Bard, D.R., et al., "A Chelating Derivative of a–Melanocyte Stimulating Hormone as a Potential Imaging Agent for Malignant Melanoma," *Br J Cancer*, vol. 62, pp. 919–922 (1990).

Cox, P.H., et al., "Technetium Labelled Somatostatin A Potential Agent for In Vivo Tumour Localization," 7th Int'l Sumpos on Radiopharm., p. 16 (1991) Abstract.

Pinski J, Shally AV, Halmos G, Szepeshazi K and Groot K: Somatostatin analogues and bombesin/gastrin–releasing peptide antagonist RC–3095 inhibit the growth of human glioblastomas in vitro and in vivo. *Cancer Res* 54:5895–5901, 1994.

Oberg K: Treatment of neuroendocrine tumors. *Cancer Treat Rev* 20:331–335, 1994.

Hoefnagel CA: Anti–cancer radiopharmaceuticals. *Anticancer Drugs* 2:107–32, 1991.

Riva P, Arista A, Sturiale C, Franceschi G et al: Possibility of control of malignant gliomas by direct intratumour or intralesional radioimmunotherapy (Abstract). *J Nuc Med* 5:144P (Abst. No. 582), 1994.

Pinski J, Schally AV, Halmos G, Szepenazi K, Groot K, O'Byrne K, Cai RZ: Effects of somatostatin analogue RC–160 and bombesin/gastrin–releasing peptide antagonists on the growth of human small–cell and non–small–cell lung carcinomas in nude mice, *Br J Cancer* 70:886–892, 1994.

Riva P, Sturiale C, Arista A, et al,: Intralesional Radioimmunotherapy of Malignant Gliomas As Adjuvant Setting In Newly Diagnosed Tumour Or As Rescue Treatment In Recurrent Lesions (Abstract). J Nucl Med Abstract Book 5:213P (Abstract No. 955), 1995.

Bender H, Zamora PO, Biersack HJ: Scintigraphy Behavior And Therapy Dose Estimates From Loco–Regionally Applied Re–188 Somatostatin Analog RC160 (Abstract). J NucL Med Abstract Book 5:183P, 184P (Abstract No. 830), 1995.

Hosono M, Haberberger T, Zamora PO et al: Imaging of Small–Cell Lung Cancer Xenografts With I–125, In–111, and Re–188 Octreotides (Abstract). J Nucl Med Abstract Book 5:72P (Abstract No. 290), 1995.

Zamora PO, Guhlke S, Bender H: Radiotherapy With Re–188–RC160, A Directly–Labeled Somatostatin Analog In Athymic Mice With PC–3 Tumors (Human Prostate Carcinoma) (Abstract). J Nucl Med Abstract Book 5:42P (Abstract No. 166), 1995.

Pimm, M.V., et al: In Labelling of A Branched Polypeptide Drug–Carrier With A Poly(L–lysine) Backbone. *Int'l J. Pharm.*, 79:77–80, 1992.

Dox et al, 1993, The Harper Collins Illustrated Medical Dictionary, p. 310.

Zamura et al, "Preparation of 188 Re–RC–160 Somatostatin Analog: A Peptide for Local Regional Radiotherapy", *Applied Radiation and Isotopes*, 1995.

% INJECTED DOSE/GRAM OF TISSUE

% INJECTED DOSE/GRAM OF TISSUE

SEQUENCE LISTING (1) GENERAL INFORMATION:

(iii) NUMBER OF SEQUENCES: 3

```
(2) INFORMATION FOR SEQ ID NO:1:

(i) SEQUENCE CHARACTERISTICS:
        (A) LENGTH: 5 amino acids
        (B) TYPE:  amino acid
        (C) STRANDEDNESS:  single
        (D) TOPOLOGY:  linear (ii) MOLECULE TYPE:  Peptide (iii) HYPOTHETICAL:  No (iv) ANTI-SENSE:  No (xi) SEQUENCE DESCRIPTION: SEQ ID NO: 1:

Ile Lys Val Ala Val
1               5

(2) INFORMATION FOR SEQ ID NO:2:

(i) SEQUENCE CHARACTERISTICS:
        (A) LENGTH: 4 amino acids
        (B) TYPE:  amino acid
        (C) STRANDEDNESS:  single
        (D) TOPOLOGY:  linear (ii) MOLECULE TYPE:  Peptide (iii) HYPOTHETICAL:  No (iv) ANTI-SENSE:  No (xi) SEQUENCE DESCRIPTION: SEQ ID NO: 2:

Tyr Trp Lys Val
1

(2) INFORMATION FOR SEQ ID NO:3:

(i) SEQUENCE CHARACTERISTICS:
        (A) LENGTH: 4 amino acids
        (B) TYPE:  amino acid
        (C) STRANDEDNESS:  single
        (D) TOPOLOGY:  linear (ii) MOLECULE TYPE:  Peptide (iii) HYPOTHETICAL:  No (iv) ANTI-SENSE:  No (xi) SEQUENCE DESCRIPTION: SEQ ID NO: 3:

Phe Trp Lys Thr
```

PEPTIDE RADIOPHARMACEUTICAL APPLICATIONS

CROSS-REFERENCE TO RELATED APPLICATIONS

This application claims the benefit of U.S. provisional Patent Application No. 60/011,027, filed Feb. 2, 1996, entitled *Ascorbate-Stabilized Radiopharmaceutical Method and Composition*; this application is also a continuation-in-part application of U.S. patent application Ser. No. 08/447,453, filed May 23, 1995, entitled *Somatostatin Radiopharmaceutical Applications*, which is a continuation-in-part application of U.S. patent application Ser. No. 08/269,929, filed Jun. 30, 1994, now U.S. Pat. No. 5,759,515 entitled *Polyvalent Peptide Pharmaceutical Applications*; which in turn is a continuation-in-part application of U.S. patent application Ser. No. 08/087,219, filed Jul. 2, 1993, now U.S. Pat. No. 5,700,444 entitled *Chemotactic Peptide Pharmaceutical Applications*; which in turn is a continuation-in-part application of U.S. patent application Ser. No. 07/840,077, filed Feb. 20, 1992, now U.S. Pat. No. 5,443,816, entitled *Peptide-Metal Ion Pharmaceutical Preparation and Method*; which in turn is a continuation-in-part application of U.S. patent application Ser. No. 07/565,275 filed Aug. 8, 1990, now U.S. Pat. No. 5,102,990, entitled *Direct Radiolabeling of Antibodies and Other Proteins with Technetium or Rhenium*; which in turn is a continuation-in-part application of U.S. patent application Ser. No. 07/391,474 filed Aug. 9, 1989, now U.S. Pat. No. 5,078,985, entitled *Radiolabeling Antibodies and Other Proteins with Technetium or Rhenium by Regulated Reduction*; this application is also related to U.S. Pat. No. 5,277,893, entitled *Direct Radiolabeling of Substrates Containing Monosulfides or Disulfide Bonds with Radionuclides*; U.S. Pat. No.5,460,785, entitled *Direct Labeling of Antibodies and Other Proteins with Metal Ions*; U.S. patent application Ser. No. 07/998,820, entitled *IKVAV Peptide Radiopharmaceutical Applications*; and U.S. patent application Ser. No. 07/998,910, entitled *YIGSR Peptide Radiopharmaceutical Applications*; the teachings of all of the foregoing which are incorporated herein by reference.

BACKGROUND OF THE INVENTION

1. Field of the Invention (Technical Field)

The present invention relates to methods of making, compositions, and uses of somatostatin-derived, peptide-based radiopharmaceuticals for the diagnosis and treatment of disease, including peptide-based metal ion-labeled somatostatin-derived compositions.

2. Background Art

Peptide-Based Radiopharmaceuticals. The use of biologically active peptides, which are peptides that bind to specific cell surface receptors or that in other ways modify cellular function, has received some consideration as radiopharmaceuticals. Biospecific imaging and radiotherapy agents started with large proteins, such as antibodies, and have evolved to antibody fragments, antigen binding domain fragments and small biologically active peptides. The smaller size of biologically active peptides confers pharmacokinetic properties, such as higher target-to-non-target ratios and faster blood clearance, which are desirable for some applications.

Several peptide-based radiopharmaceutical products are in development, including those which use somatostatin-derived peptides as an imaging agent. Radiolabeled peptide analogues of somatostatin used for diagnostic imaging include $^{123}$I-labeled Tyr-3-octreotide and $^{111}$In-DTPA-octreotide imaging agents, and research is being conducted on a variety of $^{99m}$Tc-labeled somatostatin analogues, including direct-labeled somatostatin analogues. An $^{111}$In-DTPA-octreotide product is commercially available in the United States and European countries, and is distributed by Mallinckrodt Medical, Inc.

Somatostatin and Analogues. Somatostatin is a hormone produced by the hypothalamus which normally inhibits the release of pituitary growth hormone. A number of peptide analogues have been developed which have pharmacological actions that mimic the naturally-occurring hormone. In normal subjects somatostatin and its analogues have the ability to suppress secretion of serotonin and the gastroenteropancreatic peptides, and growth hormone. Receptors for somatostatin are expressed on a variety of human tumors and their metastases. Somatostatin receptors have been found to be over-expressed in a wide range of tumor types including those arising in the brain (including meningioma, astrocytoma, neuroblastoma, hypophysial adenoma, paraganglioma, Merkel cell carcinoma, and gliomas), the digestive-pancreatic tract (including insulinoma, gluconoma, AUODoma, VIPoma, and colon carcinoma), lung, thyroid, mammary gland, prostate, lymph system (including both Hodgkin's and non-Hodgkin's lymphomas), and ovaries. Additionally, the tumors that most frequently produce percutaneous intrathoracic metastasis, including mammary gland tumors, lung carcinomas (especially small cell lung carcinomas), and lymphomas (Hodgkin's and non-Hodgkin's), all generally over-express somatostatin receptors which can be detected by scintigraphy (Krenning E P, Kwekkeboom D J, Bakker W H, Breeman W A, Kooij P P, et al: Somatostatin receptor scintigraphy with [111In-DTPA-D-Phe1]- and [123I-Tyr3]-octreotide; the Rotterdam experience with more than 1000 patients. *Eur J Nucl Med* 20: 716–731, 1993).

In spite of the high rates of over expression of somatostatin receptors on a variety of tumors, somatostatin analogues have not gained widespread clinical application for the control of cancer. Their current clinical application is primarily in the control of symptoms associated with metastatic carcinoid or VIP-secreting tumors. The somatostatin analogues have a wide therapeutic index and seem to be free of major side effects. Most of the side effects are gastrointestinal in nature and include minor nausea, bloating, diarrhea, constipation, or steatorrhea. Part of the reason for the restricted clinical use may be due to the need for long-term maintenance therapy, the consequent high cost of such therapy, and the variable effects observed in clinical settings.

Somatostatin analogues, preparation of such analogues, and uses for such analogues are known in the prior art. Such analogues are used in the treatment of certain cancers and other conditions, with one commercially available product being octreotide, manufactured by Sandoz, and sold under the trade name Sandostatin.

A wide variety of somatostatin analogues have been developed. These include RC-160, a potent somatostatin analogue originally synthesized by a team at Tulane University headed by Andrew V. Schally (Cai R Z, Szoke B, Lu E, Fu D, Redding T W and Schally A V: Synthesis and biological activity of highly potent octapeptide analogues of somatostatin. *Proc Natl Acad Sci USA*, 83:1896–1900, 1986). In recent studies conducted by Schally, among others, the effectiveness of RC-160 in inhibiting the growth of human glioblastomas in vitro and in vivo has been demonstrated. See, e.g., Pinski J, Schally A V, Halmos G, Szepeshazi K and Groot K: Somatostatin analogues and bombesin/gastrin-releasing peptide antagonist RC-3095 inhibit the growth of human glioblastomas in vitro and in vivo. *Cancer Res* 54:5895–5901, 1994.

RC-160 is a cyclic somatostatin analogue, which binds to somatostatin receptors 2 and 5 (Oberg K: Treatment of neuroendocrine tumors. *Cancer Treat Rev* 20:331–355, 1994). The general structure of RC-160 is as follows:

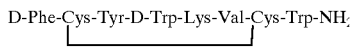

Other available somatostatin analogues include cyclic octapeptide analogues of somatostatin, such as

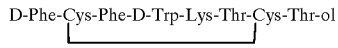

Peptide Radiolabeling. Peptides may be radiolabeled by a variety of means. Biologically active peptides for radiopharmaceuticals include that disclosed by Olexa S A, Knight L C and Budzynski A Z, U.S. Pat. No. 4,427,646, *Use of Radiolabeled Peptide Derived From Crosslinked Fibrin to Locate Thrombi In Vivo*, in which iodination is discussed as a means of radiolabeling. Peptides may be directly radioiodinated, through electrophilic substitution at reactive aromatic amino acids. Iodination may also be accomplished via prelabeled reagents, in which the reagent is iodinated and purified, and then linked to the peptide. In Morgan C A Jr and Anderson D C, U.S. Pat. No. 4,986,979, *Imaging Tissue Sites of Inflammation*, use of chelates and direct iodination is disclosed.

The utility of DTPA and EDTA chelates covalently coupled to polypeptides and similar substances are well known in the art. Hnatowich, D J, U.S. Pat. Nos. 4,479,930 and 4,668,503. DTPA has been used as a bifunctional chelating agent for radiolabeling a variety of peptides with $^{111}$In, including α-melanocyte-simulating hormone for imaging melanoma, chemotactic peptides for infection imaging, laminin fragments for targeting tumor-associated laminin receptors and atrial natriuretic peptide for imaging atrial natriuretic receptors in the kidney.

Technetium-99m is a preferred isotope for diagnostic imaging, due to its low cost, ready availability, excellent imaging properties and high specific activities. Two approaches have been described for radiolabeling proteins and peptides with $^{99m}$Tc: direct labeling and bifunctional chelates. In Dean R T, Lister-James J and Buttram S, U.S. Pat. No. 5,225,180, *Technetium-99m Labeled Somatostatin-Derived Peptides for Imaging*, direct labeling of somatostatin following reduction of native disulfide bonds resulting from cross-linked cysteine residues is disclosed. In U.S. Pat. No. 5,460,785, entitled *Direct Labeling of Antibodies and Other Proteins with Metal Ions*, referenced above, and U.S. Pat. No. 5,443,816, entitled *Peptide-Metal Ion Pharmaceutical Preparation and Method*, also referenced above, a variety of methods of direct labeling of peptides through sulfur-, oxygen- and nitrogen-containing amino acid sequences available for binding are disclosed.

A variety of high affinity chelates to bind $^{99m}$Tc to specific sites on peptides have been developed. In one approach, the bifunctional reagent is first labeled with $^{99m}$Tc, and then conjugated to the peptide. However, multiple species can result, and post-labeling purification is generally required. In another approach, a chelating agent is covalently attached to the peptide prior to radiolabeling. In Tolman G L, U.S. Pat. No. 4,732,864, *Trace-Labeled Conjugates of Metallothionein and Target-Seeking Biologically Active Molecules*, the use of metallothionein or metallothionein fragments conjugated to a biologically active molecule, including peptides, is disclosed. Other chelates which have been employed include a variety of $N_2S_2$ and $N_3S$ ligands, DTPA, and 6-hydrazinonicotinate groups.

Modes of Delivery of Radiotherapeutic Drugs. There is a need for improved methods of delivery of somatostatin-derived radiotherapeutic agents for cancer therapy because of the low absolute tumor uptake of somatostatin analogues following i.v. injection, the widespread distribution of somatostatin receptors in other tissues, and the need for highly localized therapeutic radioisotope concentrations. Some research groups have explored use of local or regional administration of radiolabeled colloid chelates and antibodies for tumor therapy (Hoefnagel C A: Anti-cancer radiopharmaceuticals. *Anticancer Drugs* 2:107–32, 1991). For example, in studies of brain glioblastomas, positive results have been obtained with direct intralesional radioimmunotherapy using $^{131}$I-labeled monoclonal antibodies (Riva P, Arista A, Sturiale C, Franceschi G et al: Possibility of control of malignant gliomas by direct intratumour or intralesional radioimmunotherapy (Abstract). *J Nucl Med* 5:144P (Abst. No. 582), 1994). With 34 evaluable patients, a median survival of 18 months was reported, versus 12 months achievable by traditional treatments, with a response rate of 38.2%, including 9 stabilized, 7 partial remission and 6 complete remission.

While use of antibodies are one treatment approach, it has become clear that another class of biologicals already possess many of the properties sought for targeting purposes. Peptide hormones and their synthetic analogues undergo high affinity interactions with target cells, and generate little or no immune response.

The targeting of somatostatin receptor-positive tumors in diagnostic imaging has a number of advantages, including the following: a) the expression of the target receptor is up-regulated in many different tumor types, and conversely the expression of receptor on normal tissues is low; b) the affinities of receptor for native hormone is high and numerous synthetic analogues which have higher affinity have been described; and c) the molecular weight of the tracer is low and circulating peptide is cleared rapidly from the circulation. The rapid clearance of the radiolabeled peptide from the circulation leads to very low backgrounds, allowing for imaging even in the face of low absolute tumor uptakes.

While it is clear that the rapid clearance of radiolabeled peptides is a considerable advantage in diagnostic imaging, it is a distinct disadvantage in targeted radiotherapy where the therapeutic effect is entirely dependent on the absolute uptake of the radionuclide at the target tumor site. Thus, intravenous administration of a radiolabeled therapeutic agent will generally not be clinically successful if the agent rapidly clears. For imaging purposes, relative uptake is important, while for therapeutic purposes, absolute uptake is important. However, local or regional administration of a radiolabeled therapeutic agent presents certain potential advantages:

a) local or regional administration sequesters and juxtaposes the peptide against the tumor, providing the highest probability of tumor binding;

b) local or regional delivery may provide a physical compartment which includes the tumor, thus maximizing time the peptide is near the tumor to provide optimal irradiation of the tumor both by direct binding and non-specific local irradiation;

c) local or regional delivery frequently involves regional clearance mechanisms including the lymphatic system, so that micrometastasis in regional lymph nodes can be irradiated; and d) local or regional delivery may provide rapid clearance from the blood stream, once the peptide has cleared to the blood stream, thereby minimizing irradiation to non-target organs.

Intra-Articular Use of Somatostatin for Treatment of Arthritis. In addition to those uses and potential uses for somatostatin and its analogues described above, research has indicated a potential use for it in the treatment of arthritis. In particular, the literature describes the passive, unradiolabeled, intra-articular use of somatostatin in treating rheumatoid arthritis. Fioravanti A, Franci A, Gelli R, Minari C, Montemerani M, Moscato P, and Marcolongo R: Evaluation of the efficacy of intra-articular administration of somatostatin in rheumatoid arthritis. *Clin-Ter.* 142(5):453–57, 1993. Another study involves the use of gold salts and somatostatin to form a new combined treatment for psoriatic arthritis. Matucci-Cerinic M, Pignone A, Lotti T, Partsch G, Livi R, and Cagnoni M: Gold salts and somatostatin: a new combined analgesic treatment for psoriatic arthritis. *Drugs-Exptl.-Clin.-Res.*, 18(2):53–61 (1992). The literature also describes radiation synovectomy using radiocolloids. See, e.g., Chinol M, Vallabhajosula S, Goldsmith S J, Klein M J, Deutsch K F, Chinen L K, Broadack J W, Deutsch E A, Watson B A, and Tofe A J: Chemistry and biological behavior of samarium-153 and rhenium-186-labeled hydroxyapatite particles: potential radiopharmaceuticals for radiation synovectomy. *J. Nucl. Med.*, 34:1536–1542 (1993). See also, Deutsch E, Brodack J W, Deutsch K F: Radiation synovectomy revisited. *Eur. J Nucl. Med.*, 45:1113–1127 (1993). Radiation synovectomy consists of the intra-articular injection of a beta-emitting radiopharmaceutical to counteract and control synovial inflammation. The use of radiocolloids has been predicated on the direct juxtapositioning of the radioactive material against the synovial membranes in joints, and by an active process of colloid uptake by the cells of the synovial membrane. In some applications, colloids are preferred over more soluble forms such as particulates, because the use of colloids helps to restrict radioactivity to the joint without leakage. Such leakage can lead to high accumulations in the regional lymph nodes, and to a lesser extent the lungs, and thereby result in unacceptable radiation to non-target organs. Use of a soluble form may therefore cause excessive, unwanted whole-body radiation. Similarly, administration via the blood may not target the appropriate cells and also lead to high non-target uptake. The concerns of practitioners have been that this treatment is expected to be a repeated treatment, and will therefore necessitate administration of radioactivity to other tissues. Some of the advantages of using [188]Re for radiation synovectomy have been described in Wang S J, Lin W Y, Hsieh B T, Shen L H, Tsai Z T, Ting G, and Knapp F F, Jr.: Rhenium-188 sulphur colloid as a radiation synovectomy agent. *Eur. J. Nuc. Med.* 22:505–507 (1995).

The Use of Ascorbate and Similar "Stabilizers" for Radiopharmaceuticals. Radiopharmaceutical compositions are known to degrade after radiolabeling by oxidation and by autoradiolysis. Some radiopharmaceuticals, such as technetium-99m and rhenium-186 or rhenium-188 labeled compounds, are known to require stabilizing agents such as antioxidants or reducing agents to maintain the radionuclide in a suitable oxidation state. Both technetium and rhenium normally exist in their highest or +7 oxidation state, which is their stable state, until they are reduced with stannous or other reducing agents in radiopharmaceutical kits. The labeled or complexed radiopharmaceutical kit becomes unstable if the complexed reduced isotope is oxidized to a higher oxidation state, releasing the bound isotope from the ligand as free (unbound) pertechnetate +7 or free perrhenate +7. Compounds such as ascorbic acid, gentisic acid, and others have been used to inhibit the oxidation of the radionuclide and/or reducing agent. In particular, the use of antioxidants, typically ascorbic and gentisic acid, is described in the literature for the purpose of extending shelf lives of low reduction-capacity, stannous-containing, radiopharmaceutical kits.

As used herein, the term "autoradiolysis" includes chemical decomposition of a peptide or protein by the action of radiation emitted from the radioisotope coupled to the peptide or protein. Autoradiolysis may be caused by the formation of free radicals in the water or other medium by the radiation emitted from the radionuclide. Free radicals are molecules or atoms containing a single unpaired electron, and exhibit high chemical reactivity. The action of antioxidants as radiopharmaceutical kit stabilizing agents involves their action as "free radical scavengers", as is generally known in the art. Ascorbic acid and gentisic acid act as free radical scavengers by donating reactive hydrogen atoms to the free radical intermediates yielding a non-reactive molecule (Kowalsky, R. J. and Perry, J. R, *Radiopharmaceuticals in Nuclear Medicine Practice*, Connecticut: Appleton and Lange 1987, 88–89). Autoradiolysis can be a significant problem with rhenium isotopes, and is typically somewhat less of a problem with technetium.

The traditional techniques of adding HSA to a composition or keeping it frozen between preparation and use are not always effective or practical for use with many radiolabeled peptides and proteins. Despite the promise shown by a number of newly-developed peptides for diagnostic and therapeutic applications, their susceptibility to autoradiolysis may limit their use. Therefore, the development of effective but non-damaging stabilizing agents is a significant and much-needed advancement in the art.

SUMMARY OF THE INVENTION

(DISCLOSURE OF THE INVENTION)

In accordance with the present invention, a method for radiolabeling a somatostatin-derived peptide analogue containing at least one disulfide bond with a radioisotope is provided. In this method, there is first provided a solution including a somatostatin-derived peptide analogue containing at least one disulfide bond. This solution is reacted with stannous ions and with a radioisotope, with a sufficient quantity of stannous ions to substantially reduce both the disulfide bonds of the peptide and the radioisotope. The radiolabeled somatostatin-derived peptide analogue is then recovered. This method may be used with a technetium radioisotope, and is particularly suitable for technetium in the form of pertechnetate. This method may also be used with a rhenium isotope, and is particularly suitable for rhenium in the form of perrhenate. The perrhenate, or a salt thereof, may be rhenium-188 and rhenium-186. The concentration of somatostatin-derived peptide analogue in the solution can be between about 25 µg and 1 mg per ml.

In the method in which perrhenate is used, the quantity of radiation may be between approximately 10 and 500 mCi, with a reaction time between approximately 1 minute and 4 hours. The labeling reaction yields the best results when the reaction occurs at a temperature from about 80° C. to about 100° C., but may be effectively labeled at lower temperatures, from about 60° C. to 80° C. The reaction proceeds even at 37° C, although slowly, and presumably would go to completion if allowed sufficient time.

In a different embodiment, a method for radiolabeling a somatostatin-derived peptide analogue containing at least one disulfide bond with a radioisotope of technetium or rhenium is provided, in which a solution including the somatostatin-derived peptide analogue is contacted with stannous ions provided to substantially and simultaneously reduce the disulfide bonds of the peptide and the radioisotope, with the radioisotope to be added later. At this step, the solution including the somatostatin-derived peptide analogue and stannous ions can be lyophilized or frozen, and stored indefinitely until radiolabeling. Radiolabeling is accomplished by reacting the solution including somatostatin-derived peptide analogue and stannous ions with a radioisotope, such as technetium and rhenium, and recovering the radiolabeled somatostatin-derived peptide analogue. If a lyophilized preparation is used, the peptide and stannous ions may be solubilized with any appropriate solvent, including normal saline, or if the radioisotope is in an aqueous solution, may be solubilized by addition of the radioisotope. The radioisotope may be technetium in the form of pertechnetate or rhenium in the form of perrhenate. The rhenium may be rhenium-188 or rhenium-186. In the method in which perrhenate is used, the quantity of radiation may be between approximately 10 and 500 mCi, with a reaction time between approximately 1 minute and 4 hours. The labeling reaction yields the best results when the reaction occurs at a temperature from about 80° C. to about 100° C., but may be effectively labeled at lower temperatures, from about 60° C. to 80° C.

Also provided in accordance with this invention is a method for treatment of regionally compartmentalized cancers within a patient, including human patients, which employs regional administration of an effective therapeutic amount of a rhenium-labeled peptide. The peptide may be somatostatin, somatostatin-derived peptide, an analogue of somatostatin or any peptide which binds to a somatostatin receptor, and which contains at least one disulfide bond, with the rhenium presumptively directly labeled into the disulfide bond in a reductive insertion wherein the Re atom is located between the two sulfur atoms. In an alternate method, regional administration may also be employed with any peptide which binds to a somatostatin receptor, including cyclic peptides which do not contain disulfide bonds. In such cases, the peptide may be labeled with rhenium or another suitable therapeutic radioisotope by any means known in the art, including use of chelates, bifunctional chelates, or other radiolabeling methods. This method may be employed with a variety of regionally compartmentalized cancers, including prostate cancer, glioblastoma, pancreatic cancer, gastric cancer, sarcomas, ovarian cancer, colon cancer, brain cancer, lung cancer, breast cancer and lymphomas. It may also be employed with regionally compartmentalized cancers which are located within a region, such as cancers within the prostate fascia, brain, peritoneal cavity, pericardium or thoracic cavity. The radiolabeled peptide may be administered by a variety of means of regional administration, including injection methods such as direct injection into the cancer, direct injection into the compartment containing the cancer and intra-arterial injection into an artery directly leading to the cancer. The method may also be used with peptide in a particulate form, including rhenium-labeled peptide in particulate form, in which case regional administration may be by an injection method including injection of the particulate form of the rhenium-labeled peptide into the compartment containing the cancer and injection of the particulate form of the rhenium-labeled peptide into an artery directly leading to the cancer.

This method may be used with radioisotopes of rhenium in the form of perrhenate, including rhenium-186 and rhenium-188. For the method in which a disulfide bond-containing peptide is used, rhenium may be directly labeled to the disulfide bond by contacting a solution including the peptide with stannous ions, with sufficient stannous ions to substantially completely reduce the disulfide bonds of the peptide and the perrhenate, and with the perrhenate, incubating the mixture of peptide, stannous ions and perrhenate to form a rhenium-labeled peptide, and recovering the rhenium-labeled peptide. In the method in which perrhenate is used, the quantity of radiation may be between approximately 10 and 500 mCi, with a reaction time between approximately 1 minute and 4 hours. The labeling reaction yields the best results when the reaction occurs at a temperature from about 80° C. to about 100° C., but may be effectively labeled at lower temperatures, from about 60° C. to 80° C.

In accordance with the present invention, there is also provided a method for increasing tumor retention of somatostatin-derived peptide analogue radiolabeled with a therapeutic radioisotope. In this method a radiolabeled somatostatin-derived peptide analogue is mixed with a serum protein component, and an effective therapeutic amount of the mixture of radiolabeled somatostatin-derived peptide analogue and serum protein component is regionally administered. The serum protein component may be gamma globulin. The means of regional administration suitable for this method includes direct injection into the cancer, direct injection into a compartment containing the cancer, and direct injection into an artery directly leading to the cancer. This method may be employed with therapeutic radioisotopes of rhenium, including rhenium-188 and rhenium-186. The somatostatin-derived peptide analogue may be directly labeled as described above, or may be labeled by any means known in the art.

The present invention, in addition to the use of various somatostatin analogs as disclosed herein, may also be used with any radiolabeled receptor-specific peptide or peptido-mimetic agent, specific for a cancer receptor. In addition to known and naturally-occurring peptides, the methods of this invention may be used with peptides derived from molecular recognition units, antibody hypervariable-region analogs, peptide sequences obtained by combinatorial or library processes, and the like. Such peptides need not be related to somatostatin, and need not be cyclic peptides. They may, by way of example, include peptides binding to a wide range of tumor-associated cell surface receptors, and preferentially cell surface receptors which are internalized upon binding. They may also include peptides binding to receptors which occur naturally, but which are over-expressed in certain cancers, such as hormone receptors. Such peptides may be labeled with any of a wide range of therapeutic radioisotopes, with $^{186}$Re and $^{188}$Re being preferred radioisotopes. Such radiolabeled peptides may be delivered by direct intra-lesion means, such as direct injection into the tumor mass, or by regional means, such as by intracavity injection into a cavity containing tumor, and by intra-arterial means, such as by injection into an artery feeding the organ containing the tumor. Administration may be by any means known in the art, including slow-bolus injection into tumors, and administration through infusion into catheters, including in-dwelling catheters, into the desired cavity or artery.

Representative cavities include the pleural, pericardial and abdominal cavities, but the methods of this invention may be used with any cavity. A wide variety of tumors may be treated, providing the tumor expresses receptors for which the peptide is specific. Examples include, in the pleural cavity, small cell lung carcinoma, lymphoma, mammary carcinoma, thyroid carcinoma and bronchial carcinoma.

In accordance with the present invention, there is also provided a method of therapy of rheumatoid arthritis by intra-articular administration of a rhenium-labeled somatostatin-derived peptide. In the preferred method an RC-160 somatostatin-derived peptide analogue is labeled with either $^{188}$Re or $^{186}$Re by any method described here or elsewhere, to result in a colloidal form of the radiolabeled preparation. Patients with rheumatoid arthritis are treated with this rhenium-labeled RC-160 colloid. The preparation is injected directly into a large joint known to be the site of an arthritic inflammation, where the colloid will lodge within the joint and surrounding bone structures. The $^{188}$Re-RC-160 is believed to act as a radiocolloid, thereby juxta-positioning the radioactivity to the synovial cells and being actively taken up by the synovial cells. However, in addition to the colloidal action, the presence of biologically active peptides (i.e., somatostatin sequences) is believed to allow direct targeting of inflammatory cells within the matrix of the inflamed joint and thereby contribute to more effective therapy with a reduced total burden of radioactivity. Repeated doses may be given as necessary. Localization of the agent, dosimetry, and other parameters may be determined by gamma camera evaluation, or similar means, utilizing the radiation of $^{188}$Re or $^{186}$Re. In other embodiments, either particulate or highly-soluble rhenium-labeled RC-160 preparations may be similarly administered. Alternatively, the preparation, whether colloid, particulate, or soluble, is injected into blood vessels leading to the joint.

In accordance with another aspect of the invention, there is provided a method of preparing a stabilized rhenium-labeled RC-160 peptide-based radiopharmaceutical composition, comprising the ordered steps of labeling said RC-160 peptide with an isotope of rhenium to form a radiolabeled pharmaceutical product, whether said labeling occurs by the methods disclosed herein or otherwise, said radiolabeled pharmaceutical product being heretofore substantially free of any stabilizing agents, and then mixing a stabilizing agent, which includes at least ascorbic acid or gentisic acid, with the radiolabeled pharmaceutical product.

Accordingly, it is an object of the present invention to provide for methods and means of labeling somatostatin-derived peptides with isotopes of rhenium, including $^{186}$Re and $^{188}$Re.

Another object of the present invention is to provide a method for the concurrent reduction of disulfide bonds in somatostatin-derived peptides and the reduction of perrhenate, thereby providing a means of labeling the peptide with isotopes of rhenium through reduced disulfide bonds.

It is a further object of the present invention to provide a means whereby the cancer-cell-killing effect of rhenium-labeled somatostatin-derived peptide is significantly greater than the effect obtained with either rhenium or the somatostatin-derived peptide alone, and is similarly greater than the effect obtained by the co-administration of rhenium and somatostatin-derived peptide.

Another object of the present invention is to provide a method for performing a therapeutic procedure by administration of a rhenium-labeled somatostatin-derived peptide into a cancerous sequestered or compartmentalized region or area, such as cancers within the brain, pleural cavity, prostate fascia or other sequestered or compartmentalized areas or regions.

Another object of the present invention is to provide a method and product which permit labeling to be accomplished by the end user using a single vial, containing a somatostatin-derived peptide and a metal ion labeling reagents, which method requires only a single step to accomplish labeling, being the introduction of the medically useful metal ion.

Another object of the present invention is to provide a method for improving the biodistribution of metal-ion labeled somatostatin-derived peptides, and metal-ion labeled peptides in general, by co-administration with agents providing for improved and favorable biodistribution and targeting of the peptide, including agents such as albumin.

Another object of the present invention is to provide for optimal pharmaceutical methods and compositions of metal-ion labeled, somatostatin-derived peptides, including optimization of phthalate buffer concentrations and pH, increasing the stability of the labeled peptide and optimizing the labeling by creating favorable conditions.

Yet another object of the invention is to provide a means whereby cancers which express somatostatin receptors can be treated through use of radioactive rhenium-labeled, somatostatin-derived peptides.

It is a further object of the present invention to provide a means whereby cancers, including prostate, breast, lung, pancreatic, brain and other cancers which significantly express somatostatin receptors, can be treated through use of a rhenium-labeled, somatostatin-derived peptide.

It is a further object of the present invention to provide a method of therapy of rheumatoid arthritis by intra-articular administration of a rhenium-labeled somatostatin-derived peptide.

It is a further object of the present invention to provide an effective method of therapy of rheumatoid arthritis wherein radioactivity is juxta-positioned to and actively taken up by the synovial cells, and biologically active peptides such as somatostatin allow for direct targeting of inflammatory cells within the inflamed joint, resulting in a reduced total burden of radioactivity.

It is a further object of the present invention to provide a method of preparing a stabilized rhenium-labeled RC-160 peptide-based radiopharmaceutical composition, using a member of the group consisting of ascorbic acid and gentisic acid as the stabilizing agent.

Other objects, advantages and novel features, and further scope of applicability of the present invention will be set forth in part in the detailed description to follow and in part will become apparent to those skilled in the art upon examination of the following, or may be learned by practice of the invention. The objects and advantages of the invention may be realized and attained by means of the instrumentalities and combinations particularly pointed out in the appended claims.

Figure 1:
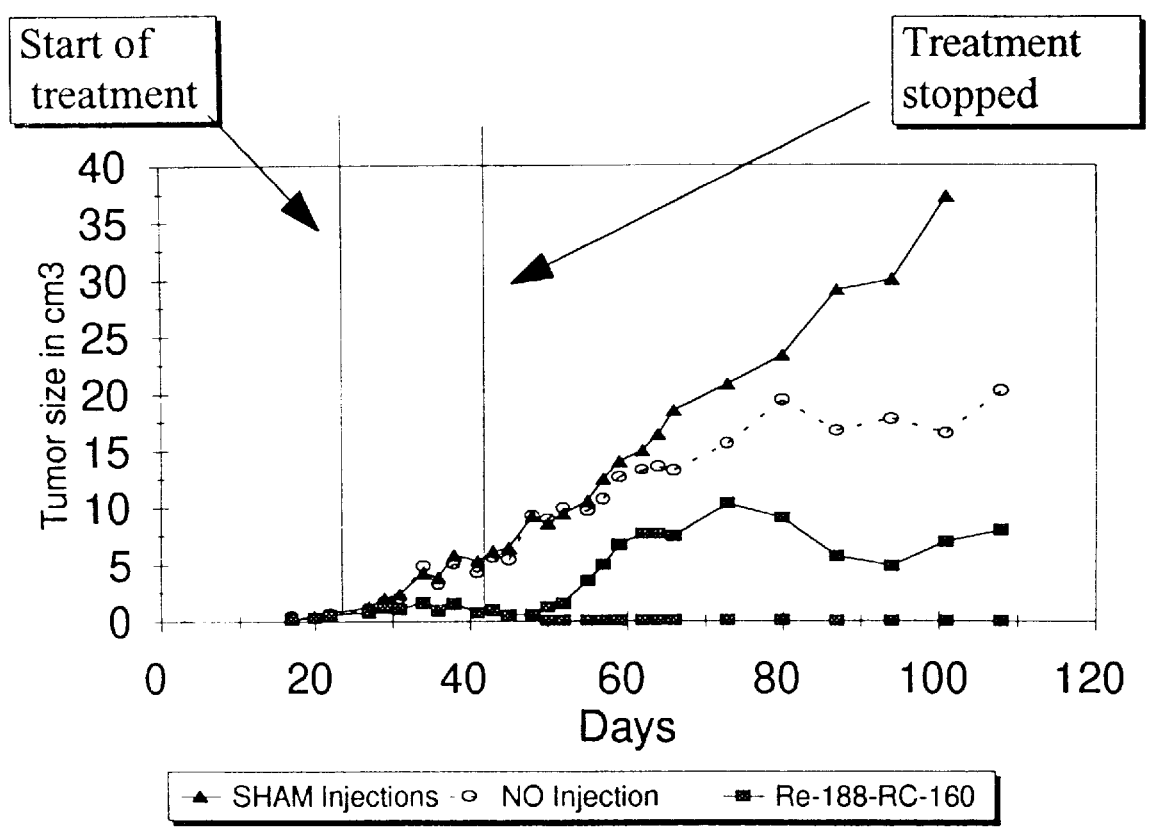
FIG. 1 shows the growth curve of PC-3 tumor xenograft tumor size, measured in cm$^3$, for animals in the initial study. Three groups of animals of 10 animals each were studied: 1) $^{188}$Re-RC-160—200 µCi in 0.2 ml injected intra-tumor on Fri, Mon, Wed, Fri, Mon, Wed, Fri, (7 doses); 2) sham injection, containing same volume and composition, but without $^{188}$Re-RC-160; and, 3) controls receiving no injections. At approximately day 45, the $^{188}$Re-RC-160 animals were bifurcated into two groups, with one group of 3 exhibiting no tumor growth, and a group of 7 exhibiting tumor regrowth.

DETAILED DESCRIPTION OF THE PREFERRED EMBODIMENTS OF THE INVENTION (BEST MODES FOR CARRYING OUT THE INVENTION)

Using the methods of this invention, somatostatin-derived peptides and a linked radiometal provide materials useful for in vivo diagnostic and therapeutic applications. When labeled with gamma-emitting radioisotopes, such as Technetium-99m ($^{99m}$Tc), such peptides can be used for diagnostic imaging of specific cell surface receptor-associated diseases or pathologies. When labeled with alpha or beta emitting radioisotopes, such as Rhenium-186 ($^{186}$Re) or Rhenium-188 ($^{188}$Re), such peptides can be used for therapy of specific cell surface receptor-associated diseases, including somatostatin-receptor positive cancers.

The terms "bind," "binding," "complex," and "complexing," as used throughout the specification and claims, are intended to cover all types of physical and chemical binding, reactions, complexing, attraction, chelating and the like.

The peptides of the invention can be:
a) naturally-occurring,
b) produced by chemical synthesis,
c) produced by recombinant DNA technology,
d) produced by biochemical or enzymatic fragmentation of larger molecules,
e) produced by methods resulting from a combination of a) through d), or
f) produced by any other means for producing peptides.

By employing chemical synthesis, the preferred means of production, it is possible to introduce various amino acids which do not naturally occur along the chain, modify the N- or C-terminus, and the like, thereby providing for greater lifetime of the peptide, improved stability and formulation, resistance to protease degradation, and the like.

The term "peptide" as used throughout the specification and claims is intended to include any structure comprised of two or more amino acids. For the most part, the peptides of this invention comprise fewer than 100 amino acids, and preferably fewer than 60 amino acids, and most preferably ranging from about 6 to 20 amino acids. The amino acids forming all or a part of the peptide may be naturally occurring amino acids, isomers and modifications of such amino acids, non-protein amino acids, post-translationally modified amino acids, enzymatically synthesized amino acids, constructs or structures designed to mimic amino acids, and the like, so that the term "peptide" includes pseudopeptides and peptidomimetics. The term "peptide" also includes dimers or multimers of peptides.

Somatostatin and somatostatin-derived peptides include peptides in which the primary biological-function domain includes the sequences Tyr-Trp-Lys-Val (SEQ. ID NO. 2), Phe-Trp-Lys-Thr (SEQ. ID NO. 3), or the like, including both L- and D-amino acid substitutions, and mimics, however composed, including peptidomimetics and other peptide-like constructs, yielding a comparable biological function domain. For somatostatin-derived peptides, the biological-function domain may also be defined functionally, as any peptide sequence which binds to one or more of the known and defined somatostatin receptors. Thus somatostatin and somatostatin-derived peptides include natural somatostatin, somatostatin-derived peptides of whatever nature, analogues of somatostatin or peptides which bind to a somatostatin receptor.

The product resulting from the methods set forth herein can be used for both medical applications and veterinary applications. Typically, the product is used in humans, but may also be used in other mammals. The term "patient" is intended to denote a mammalian individual, and is so used throughout the specification and in the claims. The primary applications of the invention involve human patients, but the invention may be applied to laboratory, farm, zoo, wildlife, pet or sport animals.

There are a number of clinical situations in which regional therapy may be a particularly attractive therapeutic option in the management of cancer, including: a) salvage therapy, e.g., in patients with small-volume residual disease after systemic chemotherapy; b) consolidation therapy, e.g., in patients with high grade tumors who achieve documented complete response after systemic chemotherapy (for which the ultimate relapse rate approaches 80%); and, c) local intensification therapy, e.g., after a limited number of courses with systemic chemotherapy for "chemical debulking", particularly with agents with known radiosensitizing properties such as 5 fluoro-uracil.

Similarly, there are a number of cancers for which local radiotherapy may be considered a particularly attractive therapeutic option, including: a) glioblastomas, b) pancreatic cancers, and c) colon cancers. Glioblastomas have a high mortality rate with few effective therapies, and usually develop as a single node in the brain. Pancreatic cancers frequently metastasize to the liver, and develop from a localized site. Similarly, colon cancers frequently metastasize to the liver, and originate in a very limited number of primary sites. Metastasis to the liver are being increasingly treated with chemotherapeutic agents by intra-arterial administration following placement of an in-dwelling catheter. The in-dwelling catheter also allows for the intra-arterial administration of the radiotherapeutic peptides of this invention. Thus, intra-arterial administration of either radiolabeled soluble somatostatin-derived peptides or radiolabeled particulate somatostatin-derived peptides may be employed.

In addition to the cancers for which local radiotherapy may be considered a particularly attractive therapeutic option, the use of radiolabeled somatostatin-derived peptide for treatment of arthritis by intra-articular administration shows promise. The use of $^{188}$Re-RC-160 as a radiopharmaceutical should be particularly applicable to joint therapy of the knee, ankle, hip, shoulder, elbow, wrist, and phalanges with applied radiation doses dependent on the size of the joint, but generally below 10 mCi. In the preferred method an RC-160 somatostatin-derived peptide analogue is labeled with either $^{188}$Re or $^{186}$Re by any method described here or elsewhere, to result in a colloidal form of the radiolabeled preparation. Patients with rheumatoid arthritis are treated with this rhenium-labeled RC-160. The preparation is injected directly into a large joint known to be the site of an arthritic inflammation, where the colloid will lodge within the joint and surrounding bone structures. The $^{188}$Re-RC-160 acts as a radiocolloid, thereby juxtapositioning the radioactivity to the synovial cells and being actively taken up by the synovial cells. However, in addition to this action, the presence of biologically active peptides (i.e., somatostatin sequences) allows direct targeting of inflammatory cells within the matrix of the inflamed joint and thereby contributes to more effective therapy with a reduced total burden of radioactivity. Repeated doses may be given as necessary. Localization of the agent, dosimetry, and other parameters may be determined by gamma camera evaluation, or similar means, utilizing the radiation of $^{188}$Re or $^{186}$Re. In other embodiments, either particulate or highly-soluble rhenium-labeled RC-160 preparations may be similarly administered. Alternatively, the preparation is injected into blood vessels leading to the joint.

The term "regionally compartmentalized" as used throughout the specification and claims is intended to include any cancer tumor which is located within a definable organ or compartment. This includes, but is not limited to tumors of specific organs, such as cancers of the brain, prostate, pancreas, liver, ovaries, colon, lung, or breast. This also includes, but is not limited to, cancers which are located within a definable compartment, such as cancers of the lymphatic system, or within the prostate fascia, brain, peritoneal cavity, pericardium or thoracic cavity. The term "regional administration" as used throughout the specification and claims is intended to include any administration method which delivers the radiolabeled, somatostatin-derived peptide to the regional compartment. This method includes injection methods such as direct injection into the cancer, direct injection into a compartment containing the cancer, and direct injection into an artery directly leading to the cancer. It also includes methods utilizing a permanent or temporary catheter, bolus delivery by any means, or other means of delivering an aqueous composition, or a composition including radiolabeled particulate somatostatin-derived peptides.

Radiolabeled particulate somatostatin-derived peptides, which may also be described as colloidal somatostatin-derived peptides or microaggregate somatostatin-derived peptides, can also be employed for therapeutic use. Certain somatostatin-derived peptides can be radiolabeled with technetium or rhenium in the particulate form, and employed as radiotherapeutic agents while in the particulate form. In particular, intra-arterial injection of particulate somatostatin-derived peptides, of a size large enough to lodge in the end of arterioles and capillaries, can be utilized in an artery feeding a tumor. By this means, it is theoretically possible to deliver highly selected end-arterial radiation which is on the order of 20 to 30 times greater than that achievable by external beam radiation. Thus, the particulate somatostatin-derived peptide allows for high selective end-arteriole or local deposition of radionuclide in the tumor. Depending on the particulate form, once the particulate somatostatin-derived peptide is at the site of the tumor, the peptide can undergo a process of slow solvation. The solvated peptide can then penetrate the tumor mass, and bind to receptors in the tumor itself. The small size of the peptide should allow for highly efficient penetration of relative avascular areas of the tumor, with any unbound peptide rapidly cleared from the body by normal elimination processes.

The metal binding sequences as found in the peptides of this invention may be stabilized by the addition of a positively-charged transition metal ion, such as Zn, Cu, Sn, Co, or Ni, and the like, selected to have a low order of binding strength. Through a replacement reaction, the transition metal ion replaces the H ion of the thiolate. The divalent ions of zinc and tin are thought to be particularly attractive. Some transition metals can simultaneously be used to reduce disulfide bridges and stabilize the metal binding sequences, such as Sn (II), which is particularly useful with cystine formations. In any case, the transition metals are weakly associated with the peptide.

The positively-charged transition metal ions are introduced to the peptide in an aqueous solution containing an appropriate buffer, which buffer also serves as a metal complexing agent or metal binding buffer. The buffer may consist of dicarboxylic acids (tartrate, phthalate, citrate), amino acids (glycine, di-glycine, tri-glycine), borate, glucoheptonate, or the like. The buffer components may also be used as stabilizers for metal ions and/or as transfer agents or ligands for radionuclides, such as $^{99m}$Tc. For radiolabeling in acidic conditions, typically 5 to 50 mM tartrate and 5 to 40 mM phthalate at pH values of about 5 to about 7 are used. For radiolabeling in basic conditions, buffers such as 10 mM glycine or glycylglycine at pH values of about 8 to about 10 are used. The buffer may also contain a number of excipients and/or stabilizers including NaCl, maltose, inositol, glucoheptonate, and the like.

The peptide of this invention is complexed with a medically useful metal ion. The medically useful metal ion may be radioactive and generate gamma rays, beta particles, or positrons which are converted into gamma rays upon collision with electrons. Alternatively, the medically useful metal ion may be paramagnetic or supramagnetic. The medically useful metal ion may be used in diagnostic imaging procedures including gamma scintigraphy, single photon emission computerized tomography, positron emission tomography or magnetic resonance imaging.

Particularly useful metal ions can be found in the group consisting of elements 26–30 (Fe, Co, Ni, Cu, Zn), 33–34 (As, Se), 42–50 (Mo, Tc, Ru, Rh, Pd, Ag, Cd, In, Sn) and 75–85 (Re, Os, Ir, Pt, Au, Hg, Tl, Pb, Bi, Po, At). Isotopes of the elements Tc and Re are particularly applicable for use in diagnostic imaging and radiotherapy. The isotope $^{99m}$Tc is particularly applicable for use in diagnostic imaging. The isotopes $^{186}$Re and $^{188}$Re are particularly applicable for use in radiotherapy. Other radionuclides with diagnostic or therapeutic applications include $^{62}$Cu, $^{64}$Cu, $^{67}$Cu, $^{97}$Ru 105Rh, $^{109}$Pd, $^{186}$Re, $^{188}$Re, $^{198}$Au, $^{199}$Au, $^{203}$Pb, $^{211}$Pb and $^{212}$Bi. The type of medically useful metal ion depends on the specific medical application. The medically-useful metal ion is selected to have a higher order of binding than the positively charged-transition metal ion used to stabilize the metal binding sequences. In the case of $^{99m}$Tc, the peptides are reacted with sodium pertechnetate which either prior to addition to the peptide, or alternatively and preferably in the presence of the peptide, is treated with a reducing agent to generate Tc with a lower oxidation state. Similarly, in the case of $^{186}$Re and $^{188}$Re, the peptides are reacted with perrhenate which either prior to addition to the peptide, or alternatively and preferably in the presence of the peptide, is treated with a reducing agent to generate Re with a lower oxidation state. In all such cases, the product of the reaction between the metal ion and the peptide is a complex of the metal ion and the peptide.

Most stannous reductions are performed at a pH of from about 5 to about 7. With amino acid side chains in a solution below pH 7, the basic amino acids are positively charged, the acidic amino acids are largely negatively charged, the alcoholic amino acids are neutral, and methionine is neutral. Since reduced rhenium or technetium binds more readily to neutral hydrogen donors rather than positively charged hydrogen donors, at the pH range 5 to 7 Cys is an optimal binding site candidate. Radiolabeling yields are dependent on pH, and are theoretically optimal at or near the $pK_a$.

In Zamora PO and Rhodes BA, U.S. Pat. No. 5,443,816, entitled *Peptide-Metal Ion Pharmaceutical Preparation and Method*, the use of peptide-based metal-ion labeled compositions as pharmaceuticals is taught, together with methods of labeling peptides, proteins and other similar substances with radiometals, paramagnetic metals and other medically useful metal ions. This invention also teaches that peptides containing a biological-function domain and a medically useful metal ion-binding domain can be labeled with medically useful metal ions for use in diagnosis and treatment of a variety of pathologic conditions. Accordingly, the teachings of this patent are incorporated herein by reference.

Somatostatin-derived peptides contain a disulfide bond. In this case, one method involves the initial reduction of the disulfide bond. In a preferred method, the following steps are employed:

a) incubating the peptide with a reducing agent to reduce some or all of the disulfide bonds to thiolate groups;

b) removing excess reducing agent from the peptide substrate containing thiolate groups;

c) adding a source of Sn (II) agent to the thiolate-containing peptide preparation in an amount sufficient to form Sn (II)-containing and sulfur-containing complexes; and, d) adding a medically useful metal ion whereby the metal ion displaces the Sn (II) in the Sn (II)-containing and sulfur-containing complexes and the metal ion and thiolate-containing peptide form metal ion-containing and sulfur-containing complexes.

The order of the steps may be altered, and the method will still produce metal ion-labeled peptides. Accordingly, the method is not limited to the order of steps presented therein. Specifically, it is possible, and in some cases advantageous, to add the Sn (II) to form Sn (II)-containing and sulfur-containing complexes prior to removing excess reducing agent from the peptide substrate. In this way, oxidation of thiolate groups or reformation of disulfide bonds and other cross-linkages is immediately minimized.

The quantity of Sn (II) provided must also, if pertechnetate ($TcO_4$) or perrhenate ($ReO_4$) is the metal ion, be sufficient to reduce the pertechnetate or perrhenate to the desired redox state. If the foregoing method is employed for pertechnetate or perrhenate, then sufficient Sn (II) may be added in step c) to reduce the metal ion, the radiometal to be added in a subsequent step. Alternatively, additional Sn (II) may be added at any time either prior to or concurrent with introduction of the metal ion. For example, if Sn (II) is added to form Sn (II)-containing and sulfur-containing complexes prior to removing excess reducing agent from the peptide substrate, then additional Sn (II) would be added subsequent to removal of the excess reducing agent. Similarly, if Sn (II) is employed as the initial reducing agent in step a), and excess Sn (II), stannic, and other impurities removed, then sufficient additional Sn (II) would be added in step c), or concurrently with introduction of the metal ion, and in a quantity sufficient to reduce the metal ion to the desired redox state.

Numerous reducing agents have been described and are known to those skilled in the art. Particularly useful types of reducing agents include 2-mercaptoethanol; 1,4-dithiothreitol; 2,3-dihydroxybutane-1,4-dithiol; 2-aminoethanethiol HCl; thioglycolate; cysteine; reduced glutathione; $Na_2SO_3$; Sn (II); Cu (I); and Ti (II). The reducing agent may be dissolved in a solute or may be attached to a solid phase. Reducing agents attached to a solid phase are commercially available, and methods for their use are known to those skilled in the art. The degree to which the peptide requires disulfide bond reduction depends on the nature of the peptide and its intended medical application. Generally speaking, milder reduction conditions and shorter incubation periods are normally employed than are required to reduce disulfide bonds in proteins or complex polypeptides, such as antibodies. In any event, reduction is halted before excessive fragmentation of the peptide or loss of the biological-function of the peptide occurs.

In one specific embodiment, Sn (II) is used as a reducing agent at a concentration of 5 mM. In this embodiment the Sn (II) is dissolved in a buffer composed of approximately 10 mM tartrate and 40 mM phthalate, pH 5.5, and the Sn (II) buffer admixed with a peptide substrate at a concentration of 8.3 mg/mL. The reduction reaction is allowed to proceed for a period of time at room temperature, three hours having been employed successfully with some peptides containing a single disulfide bond, after which time the reaction is terminated by removing excess Sn (II) ions by chromatography.

Removal of the reducing agent, whether Sn (II) or some other reducing agent, can be accomplished by a variety of suitable means, including such methods as dialysis, ultrafiltration, positive-pressure membrane filtration, precipitation, preparative high performance liquid chromatography, affinity chromatography, other forms of chromatography and preparative isoelectric focusing. Many of the reducing agents contain thiols, which if present in the final labeling mixture, can complex with the medically useful metal ion. Such complexes can have severe and unknown side effects if administered in vivo. Additionally, some reducing agents exhibit unacceptable toxicity. Thus removal of the reducing agent both limits the degree of reduction to that desired, as well as providing for increased utility and safety of the labeled preparation by removal of toxic or otherwise undesirable reducing agents.

Thiolate groups in reduced peptides are highly reactive and can interact to reform disulfide bonds. The use of Sn (II) as a protectant is believed to minimize the reformation of disulfide bonds. Sources of Sn (II) include stannous tartrate, stannous glucoheptonate, stannous gluconate, stannous phosphonate, stannous chloride, stannous sulfate, stannous acetate, and stannous fluoride. The selection of the source of Sn (II) and its final concentration depends on the intended medical application of the peptide, the nature of the peptide, the relative and absolute number of thiolate groups and the metal ion to be used. In one embodiment stannous tartrate is used at a concentration of 1.25 mM. The stannous tartrate is added to the peptide after removal of the peptide-reducing agent. The stannous tartrate is prepared in a buffer composed of 10 mM tartrate and 40 mM phthalate, pH 5.6, and is added to peptide to yield a final concentration of 1 mg/mL peptide solution.

The concentration of stannous and total tin varies depending on the metal ion to be used. For example, a significantly higher stannous concentration is required to reduce perrhenate than to reduce pertechnetate. $^{188}$Re in the form of perrhenate may be labeled using kits with between about 2.5 to 15 mM stannous, with total tin correspondingly ranging from about 1 to 5 mg or higher if a larger volume kit is employed, all at a pH of between about 5 and 6. Generally speaking, lower stannous concentration kits require heating, such as for 30 to 60 minutes in a boiling bath, to effectively reduce all the available perrhenate, while high total tin kits have sufficient reduction capacity to reduce the perrhenate within about one hour when incubated at room temperature. Increasing the stannous concentration above about 15 mM has negligible effects on reduction capacity, and at higher concentrations it becomes increasingly difficult to keep the stannous in solution.

In an alternative method, it is possible to employ a method which involves concurrent reduction of both the disulfide bond in the peptide and the metal ion. This method is particularly advantageous when using metal ions such as rhenium, given that perrhenate requires, as compared to pertechnetate, substantially greater reduction conditions. In a preferred method, the following steps are employed:

a) mixing the peptide with a reducing agent capable of reducing disulfide bonds to thiolate groups, and concurrently reducing metal ions to a desired redox state;

b) adding the metal ion, such that concurrent reduction of disulfide bonds of the peptide and reduction of the metal ion are initiated, such as by adding an aqueous metal ion preparation to a lyophilized or otherwise dried mixture of peptide and reducing agent;

c) permitting the reaction to go to completion, whereby the reducing agent reduces the disulfide bonds, resulting in thiolate-containing peptide, and the metal ion, and the metal ion and thiolate-containing peptide form metal ion-containing and sulfur-containing peptide complexes. If Sn (II) or another suitable transition metal with reduction potential is employed as the reducing agent, then the disulfide bond reduction process may result in Sn (II)-containing and sulfur-containing peptide complexes, and the metal ion displaces the Sn (II) in the Sn (II)-containing and sulfur-containing complexes, and the metal ion and thiolate-containing peptide form metal ion-containing and sulfur-containing peptide complexes.

The order of the steps may be altered, and the method will still produce metal ion-labeled peptides. Accordingly, the claims are not limited to the order of steps presented therein. Specifically, it is possible, and in some cases advantageous, to add the metal ion to the peptide prior to adding the Sn (II), so that steps a) and b) are reversed. It is also desirable to avoid oxidation of the preparation, so that the reactions occur in an essentially oxygen-free environment. This may be done, in part, by purging all solutions with inert gases such as nitrogen or argon, and performing all reactions under an inert gas atmosphere.

Using this method, and depending on the radiolabel to be employed, the amount of stannous employed can significantly vary. The concentration of stannous and total tin varies depending on the metal ion to be used. For example, a significantly higher stannous concentration is required to reduce perrhenate than to reduce pertechnetate. $^{188}$Re in the form of perrhenate may be labeled using kits with between about 2.5 to 15 mM stannous, with total tin correspondingly ranging from about 1 to 5 mg or higher if a larger volume kit is employed, all at a pH of between about 5 and 6. Generally speaking, lower stannous concentration kits require heating, such as for 30 to 60 minutes in a boiling bath, to effectively reduce all the available perrhenate, while high total tin kits have sufficient reduction capacity to reduce the perrhenate within about one hour when incubated at room temperature. Increasing the stannous concentration above about 15 mM has negligible effects on reduction capacity, and at higher concentrations it becomes increasingly difficult to keep the stannous in solution.

For both $^{186}$Re or $^{188}$Re labeling, approximately 5 mM of stannous tartrate, for a total tin concentration of approximately 1.2 mg, was employed with 200 μg of peptide. For labeling the same quantity of peptide with $^{99m}$Tc, approximately 0.5 mM of stannous tartrate was employed. The amount of Sn (II) in the preparation must be such as to be sufficient to completely reduce the metal ion to the desired redox state under the specified reaction conditions, without having such Sn (II) concentrations that the tin precipitates from the solution. Precipitation can be, in large part, controlled by the selection of appropriate buffers. The quantity of Sn (II) also varies with the reaction conditions; for example, with preparations which are incubated at temperatures in the range of 80° C. to 100° C., less Sn (II) is required than if incubation is effected at room temperature. The incubation time also varies depending on the incubation conditions, principally temperature, although pH and other conditions also affect incubation time. Generally speaking, incubation at temperatures in the range of 80° C. to 100° C. are substantially shorter than incubations at room temperature, requiring an incubation period from one-half to one-tenth or less in length.

Regardless of the method employed, addition of high molar ascorbic acid to the rhenium-labeled RC-160 post-labeling has a marked effect of increasing resistance to radiolytic decomposition of the kit. Methods and techniques for adding ascorbate or gentisic acid to the composition are described in greater detail below.

One kit formulated for use with the somatostatin-derived peptide RC-160, which peptide is described in greater detail below, contained 200 μg of peptide and 5 mM of stannous, or 1.2 mg total tin, at pH 5.0. When labeled by addition of $^{188}$Re as perrhenate and heating for 1 hour at 90° C., perrhenate reduction and radiolabeling was essentially 100%. Total colloid was less than 3%, and unbound perrhenate was less than 0.5%. When labeled with reactor-produced, low specific activity $^{186}$Re as perrhenate (2.5 to 5 mCi/μg), the kit had sufficient reduction capacity to yield comparable results.

For labeling with pertechnetate, it is possible to use between 0.2 and 1 mM of stannous, and preferably from 0.5 to 1 mM stannous, with total tin as low as 40 μg, depending upon the fill volume.

Regardless of the method employed, the form of stannous employed depends in part on the buffers utilized in the kits. For examples, in kits with buffers containing tartrate as a complexing agent, use of stannous tartrate salt is desirable. For kits containing complexing agents other than tartrate, such as kits containing EDTA, stannous chloride dihydrate may be employed. Generally speaking, all stannous is added in concentrated hydrochloric acid. This favors maintaining the tin in the Sn (II) oxidation state, as stannous ions, rather than the Sn (IV) state, as stannic ions. Sn (II) effectively reduces radiometals such as pertechnetate or perrhenate, while Sn (IV) does not. Complexing agents are generally used in a 2 to 20 molar excess over the total tin, to insure that all of the tin, including both stannous ion and any stannic ion, will be complexed. Uncomplexed tin at neutral pH readily forms an insoluble hydroxide. In the absence of complexing agents, above pH 5.5 colloidal tin species may be formed before the hydroxide precipitates. Complexing agents sequester tin from the hydrolysis reaction, but do not prevent tin from entering into redox reactions. pH titrations of stannous solutions have shown increasing complexing ability with EDTA>>citrate>>glucoheptonate>>tartrate>>malic acid. Though stannous tartrate exists as a 1:1 molar ratio of tin:tartrate as the dry salt, empirical evidence suggests that a minimum 2-fold excess of tartrate is necessary to stabilize stannous at neutral pH. However, EDTA, citrate and glucoheptonate can all stabilize stannous at approximately 1:1 molar ratios at neutral pH; a working formula of 1.2:1 molar ratio of complexing agent:stannous can be satisfactorily utilized.

Regardless of the method employed, high concentrations of tin may be stabilized through the use of appropriate buffers. For example, metal binding buffers, such as diglycine and triglycine at 50 to 100 mM, can increase the stability of high millimolar tin concentrations at neutral pH. For example, a buffer containing 50 mM diglycine or triglycine, with an appropriate complexing agent such as EDTA, citrate, glucoheptonate or tartrate, can be used to stabilize the tin, and prevent precipitation, when the total tin concentration is in the range of 5 to 10 mM. Suitable metal ion buffers include citrate and tartrate, polyaminocarboxylic acids such as EDTA, DTPA and NTA (nitrilotriacetic acid), ACES (N-2-acetamido-2-aminoethanesulfonic acid, ADA (N-2-acetamidoiminodiacetic acid), bicine, tricine, glycylglycine, triglycine, tetraglycine, and MES (2-(N-morpholino)ethanesulfonic acid). For example, it is possible to stabilize a high millimolar stannous solution, comprising 5 mM stannous tartrate in 40 mM KH Phthalate and 10 mM NaK tartrate, at neutral pH and above by addition of a second metal binding buffer, such as glycylglycine, which has a pKa of 8.2, at concentrations from 50 to 100 mM. Generally speaking, the solubility of stannous is enhanced by addition of a second metal binding buffer which has a pKa at or close to the pH of the composition to be radiolabeled. For example, if a radiolabeling composition contains tartrate, which has a pKa of 4.3, and if the composition is to be radiolabeled at a pH significantly different from 4.3, then increased tin complexation, with resultant stability of the tin and protection from precipitation, can be achieved by addition of a second metal binding buffer with a pKa at or near the pH of the composition to be radiolabeled.

Depending on the somatostatin peptide employed, formulation and reaction conditions must be altered. For example, work was done using a somatostatin-derived peptide called RC-160 or Vapreotide, and supplied by Debiopharm S. A. of Switzerland. RC-160 is a cyclic somatostatin analogue, which is reported to bind to somatostatin receptors 2 and 5 (Oberg K: Treatment of neuroendocrine tumors. *Cancer Treat. Rev.* 20:331–355, 1994). This peptide has the structural formula

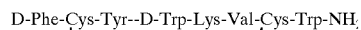

RC-160 was used as both the glutamate and acetate salt for radiolabeling. RC-160 was initially radiolabeled with $^{99m}$Tc and $^{188}$Re by a two-step method. The peptide disulfide bond was reduced by heating in the presence of stannous ion and complexing agent as stannous tartrate in the first step. $^{99m}$Tc sodium pertechnetate or $^{188}$Re sodium perrhenate was then added and the preparation further heated to radiolabel in a second step.

During radiolabeling, RC-160 undergoes a phase transition from a soluble form to a colloidal form dependent on the pH of the solution. Thus, at pH 6 or higher a colloid is formed, while at pH 5.5 or less the peptide remained soluble. The colloidal material is formed only when RC-160 is present in the solution, and does not arise when some other peptides are used or when peptides are not used at all. The colloidal $^{188}$Re-RC-160 can be dissolved in ethanol or by simple re-heating to 100° C. This indicates that the colloid results from the complexation of tin ions with $^{188}$Re and RC-160, and does not arise from precipitation of tin salts. The decreased solubility of the peptide is believed to be due to charge neutralization of the peptide.

The kit tartrate concentration was then increased from 10 mM to 50 mM, at pH 5.0. This gave a final kit molar ratio of 10:1 tartrate complexing agent:stannous. The original kit buffer, potassium hydrogen phthalate, was lowered from 40 mM to 10 mM. It was observed that phthalate is necessary in the kit to yield a single radiolabeled peak by HPLC analysis. Potassium hydrogen phthalate at the lower 10 mM concentration was found to be sufficient for this purpose while affording a higher glass transition temperature for facile freeze drying. Maltose was added as a freeze-drying excipient.

Regardless of the particular method of preparation employed, the addition of high molar ascorbic acid to the rhenium labeled RC-160 kit post labeling has a marked effect of increased resistance to radiolytic decomposition of the kit. Inclusion of ascorbic acid into the kit formulation prior to labeling has a detrimental effect on radiolabeling yields, even when ascorbate is also later added in after radiolabeling. The labeling reaction of reduced rhenium with the somatostatin analogue RC-160 is adversely affected in the presence of either ascorbic acid or sodium sulfite, a common antioxidant.

The invention is further illustrated by the following non-limiting examples.

EXAMPLE 1—RADIOLABELING OF SOMATOSTATIN PEPTIDE ANALOGUE CONTAINING DISULFIDE BOND

The peptide is a cyclic octapeptide analogue of somatostatin. The biological-function portion of the molecule is associated with the Phe-D-Trp-Lys-Thr portion of the molecule. The disulfide bridge between the two cysteine residues is reduced using an Sn (II) reducing agent, presumptively forming sulfur-tin complexes. The peptide was obtained in acetate buffer pH 4.4. To the peptide containing solution was added (1:1) 10 mM tartrate/40 mM phthalate buffer, pH 5.6 (P/T buffer), to result in a solution containing 500 μg of peptide/ml. This solution was mixed (1:1) with P/T buffer containing 1.25 mM stannous tartrate, and allowed to incubate at room temperature for at least three hours. Aliquots of 0.5 ml were then dispensed into individual vials. Each kit contained 0.25 mg of peptide, 40 mM phthalate, 10 mM tartrate, and 44 μg of stannous tartrate. All solutions were purged with nitrogen prior to use and all preparations made under an anaerobic atmosphere. The peptide in the labeling kits was labeled with $^{99m}$Tc by addition of 1–2 mCi of sodium pertechnetate (U.S.P.) and allowing the reaction to proceed for 30 minutes.

EXAMPLE 2—PREPARATION, LABELING AND EVALUATION OF SOMATOSTATIN-DERIVED PEPTIDE RADIOLABELING KITS

Three somatostatin-derived peptides were prepared as radiolabeling kits, RC-160, octreotide and (β-(2-naphthyl)-cyclic2,7-D-Ala-Cys-Tyr-D-Trp-Lys-Val-Cys-Thr-amide). RC-160 was supplied by Debiopharm SA (Lausanne, Switzerland) and octreotide was obtained as Sandostatin 500 (Sandoz, Switzerland).

$^{99m}$Tc-Labeling Kits. The kits intended for radiolabeling with $^{99m}$Tc contained 0.4 ml final volume with 100 μg of peptide, 10 mM tartrate, 40 mM phthalate (pH 5.6), and 1.25 mM stannous tartrate. In some cases, maltose and glycine were used as excipients, such as 2% maltose and 50 mM glycine. The kits were sealed under an atmosphere of nitrogen, allowed to incubate for 4 hours at room temperature, and then stored at −30° C. For radiolabeling, a vial was thawed to room temperature and pertechnetate solution added. All radiolabelings were initiated by adding 0.6 ml of pertechnetate solution (5–15 mCi), and subsequently heating the solution at 100° C. for 30 minutes.

To prepare the RC-160 kits, the peptide was dissolved in nitrogen-purged water to a concentration of 500 μg/ml. To the peptide solution was added an equal volume of a 2× concentrate of buffer solution (pH 5.6). After mixing, the solution was filtered through a 0.22 micron filter directly into 1 ml capacity amber vials so that each vial contained 0.4 ml. The vials were sealed under an atmosphere of nitrogen, allowed to incubate for 4 hours at room temperature, and stored frozen at −30° C.

Rhenium Labeling Kits. The radiolabeling kits for use with $^{188}$Re typically contained a final volume of 2.0 ml with 500 μg peptide in a buffer solution of 20 mM tartrate and phthalate (pH 5.6) and 5 mM stannous tartrate (pH 5.6). In these kits, maltose and glycine were used as excipients. The kits were allowed 4 hours to incubate at room temperature prior to freezing. During the incubation period, a white flocculent formed in the RC-160 kits, but not in the octreotide kits. The flocculent was found to be the peptide and could be solubilized by the addition of 0.6 ml of ethanol. Radiolabeling was initiated by adding 2.0 ml of perrhenate solution, and subsequently heating the solution at 100° C. for 30 minutes. The radiolabeled peptides were diluted with pre-filtered 20% human serum albumin. These solutions of peptide in albumin showed no signs of precipitation even upon cooling and overnight storage at 4° C.

Radiochemical Evaluation. Both peptides were found to be easily radiolabeled with labeling efficiencies greater than 95% for the $^{99m}$Tc and $^{188}$Re variants as determined by TLC. Reverse phase chromatography using $C_{18}$ SepPaks confirmed high labeling efficiency, as did analytical RP-HPLC. $^{99m}$Tc-RC-160 and $^{99m}$Tc-octreotide remained at the origin of silica-coated TLC strips (ITLC-SG) when saline was used as the mobile phase and migrated with or near the solvent front when 85% ethanol was used as mobile phase. This behavior was also observed with $^{188}$Re-RC-160, $^{188}$Re-octreotide, $^{131}$I-RC-160, and $^{125}$I-(Tyr$^3$)-octreotide. A small amount of $^{99m}$Tc remained at the origin when using 85% ethanol as the mobile phase and may represent $^{99m}$Tc-or $^{188}$Re-colloids. The TLC of $^{188}$Re-RC-160 and $^{188}$Re-octreotide demonstrated that the radiometal incorporations were essentially 100%, with no detectable radiocolloid formation.

Analytical reverse phase HPLC using a $C_{18}$ column eluted with a continuous gradient of acetonitrile and analyzed by a post-column radioisotope detector indicate only a small amount of unbound $^{99m}$Tc eluting in the void volume and a single large peak of radioactivity eluting at approximately 25 minutes (flow rate 1 ml/minute). The chromatographic recoveries were greater than 95%. The low amount of peptide used in the analysis (0.20 μg) did not allow for effective monitoring by $A_{280}$. However, the $^{99m}$Tc-RC-160, $^{188}$Re-RC-160 and radioiodinated RC-160 all eluted at the same time and position.

$^{99m}$Tc-labeling. RC-160 and octreotide were both easily and reproducibly radiolabeled with $^{99m}$Tc as determined by TLC and reverse-phase chromatography. In a series of time studies, labeling of either RC-160 or octreotide was essentially completed by 15 minutes, and a time of 30 minutes was selected for further studies. The radiolabelings were conducted over a temperature range (room temperature, 37° C., 70° C., and 100° C), and subsequently heating at 100° C. for 30 minutes was selected for most studies. Heating resulted in a more uniform radiolabeled product as determined by analytical HPLC. Using this format, both RC-160 and octreotide could be routinely radiolabeled with 5–15 mCi of $^{99m}$Tc with incorporations greater than 95%.

$^{188}$Re-labeling. RC-160 and octreotide were also radiolabeled with $^{188}$Re. An increase in the amount of stannous ion was found, however, to be needed to reduce the subsequently added $^{188}$Re. As with the $^{99m}$Tc, a labeling time of 30 minutes was determined to be optimal based on a kinetic study involving several time points and analysis by reverse phase HPLC. Using this format, RC-160 and octreotide were radiolabeled with 6–8 mCi of $^{118}$Re with incorporations greater than 95%.

The pre-incubation in stannous ions of RC-160 for 4 hours at room temperature in 5 mM stannous tartrate resulted in an insoluble peptide derivative. Such a precipitate was not formed with octreotide. Such a precipitate was not optically observed in the $^{99m}$Tc labeling kits where 1 mM stannous tartrate was used to reduce subsequently added $^{99m}$Tc. The precipitation was time dependent as the initial mixture was clear and stayed optically clear for at least 1 hour after initial formulation.

The precipitated RC-160 was solubilized in 30% ethanol and in this form was radiolabeled with either $^{99m}$Tc or $^{188}$Re. The precipitated peptide could also be radiolabeled in its precipitated form with $^{99m}$Tc or $^{188}$Re, but remained optically insoluble. Upon dilution (1:1) with 20% human serum albumin, the peptide stayed in solution even upon cooling.

EXAMPLE 3—PREPARATION OF LABELING KIT FOR CONCURRENT REDUCTION OF DISULFIDE BONDS AND METAL ION

A somatostatin-derived peptide kit was formulated using the RC-160 somatostatin analogue described above. The final kit formulation for rhenium labeling kits was as follows:

| | |
|---|---|
| RC-160 | 200 micrograms |
| maltose | 1% |
| sodium potassium tartrate | 45 mM |
| potassium hydrogen phthalate | 10 mM |
| stannous tartrate | 5 mM |
| total tin | 1,187 micrograms |
| pH | 5.0 |
| Fill volume | 2.0 ml |

For $^{99m}$Tc labeling kits, the formulation was the same, except that those kits contained only 0.5 mM stannous tartrate.

The formulation was aliquoted into 5 ml serum vials, which were then immediately loaded into a freeze dryer under argon. The shelf temperature was initially between 0° and 5° C., and was lowered to −50° C. for 2 hours prior to commencing the lyophilization cycle. Primary drying was at a shelf temperature of −40° C. for 16 hours, followed by 4 hours at −10° C., both at a chamber pressure set at 0 mTorr and condenser temperature set at −55 ° C. Secondary drying was at a shelf temperature of 35 ° C. with the drying chamber pressure set to 0 mTorr for at least 8 hours with the same condenser temperature. The drying chamber was then backfilled with argon, the kits stoppered and stored at 0–5 C.

EXAMPLE 4—RADIOLABELING OF SOMATOSTATIN PEPTIDE KITS FOR CONCURRENT REDUCTION OF DISULFIDE BONDS AND METAL ION

The vialed kits of Example 3, containing 1.187 mg of total tin, were labeled with both $^{188}$Re and $^{186}$Re. To label with $^{188}$Re, $^{188}$Re sodium perrhenate obtained from an experimental $^{188}$W/$^{188}$Re generator system developed at Oak Ridge National Laboratory was used (Knapp F F Jr, Mirzahdeh S, Beets A L, Sharkey R, Griffiths G, Juweid M, and Goldenberg D M: Curie-scale tungsten-188/rhenium generators for routine clinical applications, In: *Technetium and Rhenium in Chemistry and Nuclear Medicine*, (eds) M Nicolini, G Bandoli, U Mazzi; S G Editoriali, Padova, Italy, 1995, pp 319–324), and was diluted with saline for injection to the vial fill volume of 2 ml. The vial was then placed in a boiling bath for 60 minutes, following which it was subjected to testing.

To label with $^{186}$Re, reactor produced $^{186}$Re was obtained from Oak Ridge National Laboratory, and the desired millicurie amount was diluted with saline for injection to the vial fill volume of 2 ml. The vial was then placed in a boiling bath for 60 minutes, following which it was subjected to testing.

For both kits, reverse phase HPLC analysis shows a single radiolabeled peak on the radiolabeled RC-160 peptide. Percent radiolabeled colloid was determined by instant thin layer chromatography on silica gel strips developed in 85% ethanol and 15% aqueous acetic acid at pH 3.5, colloid Rf=0.0, and showed less than 5% colloid. Percent unbound rhenium was determined on silica gel developed in 0.15 M NaCl, Rf=1.0, and showed less than 1% unbound rhenium. The lipophilic radiolabeled RC-160 migrates with the solvent front in ethanol and acetic acid and remains at the origin in 0.15 M NaCl.

Cysteine challenges of the labeled kit were performed to determine the peptide-metal bond strength by displacement with cysteine. The millimolar concentration of cysteine necessary to displace 50% of the labeled activity was 40 mM cysteine for rhenium labeled RC-160. Technetium labeling kits were formulated according to the method of Example 3, but containing lower stannous content as specified. The technetium labeling kits were labeled as set forth above, using $^{99m}$Tc sodium pertechnetate. When subjected to cysteine challenge, only 5 mM cysteine was required to displace 50% of the labeled activity, indicating that the metal to peptide bond for rhenium labeled RC-160 is 8 times as strong as the technetium labeled RC-160 when challenged with cysteine.

EXAMPLE 5—INTRATUMOR INJECTION BIODISTRIBUTION IN ANIMAL MODELS

The rapid clearance from the blood of $^{188}$Re-RC-160 or $^{99m}$Tc-RC-160 (T½=2–5 minutes) demonstrated in normal and xenografted nude mice suggested that only a low absolute uptake of radiolabel could be expected from an intravenous injection. Using dynamic imaging techniques followed by serial static imaging, the loco-regional behavior of $^{99m}$Tc-RC-160 (surrogate for $^{188}$Re-RC-160) was examined. Direct intratumor injection resulted in biological half lives of 12–14 hours whereas pertechnetate or perrhenate with no peptide had a biological half life of 0.5–1 hour. When $^{99m}$Tc-RC-160 or pertechnetate was injected into normal tissue (muscle) the biological half life was 0.5 hours and 5 minutes, respectively. Intra-cavity injections which could be used for regional application resulted in different retention times. Injection into the pleural cavity resulted in a biological half life of 6.4 hours. Injection into the abdominal cavity resulted in a half life of 3.7 hours.

Local administration by intratumor injection and biodistribution in athymic mice with human prostate tumors. Biodistribution studies with $^{188}$Re-RC-160 injected as both microparticles, prepared by the method of Example 2, but without the addition of an alcohol to solubolize the peptide, or in soluble form, prepared by the method of Example 2, were performed in athymic mice bearing xenografts from the human prostate tumor cell line PC3. PC3 is a metastasis-derived, androgen-independent, poorly-differentiated prostate adenocarcinoma cell line, and thus the experimental model is of an advanced human cancer.

At two hours after injection, nearly 30% of the injected dose was resident in the tumor when $^{188}$Re-RC-160 was injected in microparticle form, whereas with the soluble form approximately 12% was in the tumor. Most of the rest of the radioactivity was found in the gut (stomach, small intestine, and large intestine) consistent with the known route of excretion via the liver. The liver had approximately 4% of the injected dose per gram of tissue. Only small amounts of radioactivity were found in any other organ examined including the pancreas and brain. There was very little uptake in the spleen or bone.

By 6 hours after injection, the amount of material still in the tumor was approximately 30% for the microparticle form and 10% for the soluble form. By 24 hours, the amount in the tumor had decreased to about 10% and 4% for the microparticles and soluble material, respectively.

Biodistribution of negative control and reference compounds in tumor-bearing mice. $^{188}$Re-perrhenate ([ReO$_4$]$^-$) and $^{188}$Re-mercaptoacetyl-triglycine ($^{188}$Re-MAG3) were used to evaluate the non-specific tumor retention of $^{188}$Re upon direct injection into the tumor. Neither of these compounds was retained to any substantial degree by the tumor when examined 6 hours after injection. The amount of radioactivity in the tumor for $^{188}$Re-perrhenate was 0.49% I.D./gm±0.27% I.D./gm (S.E., n=5) whereas the amount of $^{188}$Re-MAG3 in the tumor was 0.05% I.D./gm±0.01% I.D. (S.E., n=5). In the case of perrhenate, only the kidneys (organ of clearance) and the thyroid were found to have a substantial amount of radioactivity. In the case of $^{188}$Re-MAG3, only the pancreas, kidney (organ of excretion), and to a lesser extent the spleen evidenced uptake. The uptake in the pancreas was thought to be within experimental error. I-131-RC-160 was used as a positive control reference compound and 6 hours post-injection the biodistribution was found to be generally similar to that observed with $^{188}$Re-RC-160 as follows: a) significant amounts of radioactivity were found in the tumor (23.1% I.D./gm±10.4% S.E., n=5); b) the amount of radioactivity in the blood was low (0.8% I.D./gm±0.2%); c) radioactive material appeared to clear through the liver to the gastrointestinal tract; and, d) little radioactivity was found in organs other than those in the gastrointestinal tract and thyroid.

In Vivo Competition of Somatostatin Analogues. Experiments were conducted to determine if $^{188}$Re-RC-160 could be displaced with unlabeled somatostatin analogues. Animals were concurrently injected with a trace amount of $^{188}$Re-RC-160 and either unlabeled octreotide or unlabeled RC-160. The unlabeled material was in significant excess to the amounts of $^{188}$Re-RC-160 administered, and the unlabeled material was administered both i.p. and by intratumor injection. The levels of radioactivity found in the tumors at 6 hours post injection were reduced, compared to the level obtained with injection of $^{188}$Re-RC-160 alone, by approximately 80% for octreotide, and 70% for RC-160. The average percent injected dose/gram for tumor tissue was over 10% for $^{188}$Re-RC-160 alone, and was 1.9%±0.5% for $^{188}$Re-RC-160 administered with octreotide, and 3.0% ±0.8% for $^{188}$Re-RC-160 administered with unlabeled RC-160 (S,E., n=5). The overall pattern of biodistribution was similar in all treatments, except for the amount retained in the tumors, with apparent clearance through the gastrointestinal tract and little if any accumulation in other organs. Thus, both unlabeled octreotide and unlabeled RC-160 appear to compete for the same receptor-binding sites in vivo, demonstrating the receptor-based binding of $^{188}$Re-RC-160.

EXAMPLE 6—COMPARATIVE BIODISTRIBUTION OF SOMATOSTATIN ANALOGUES RC-160 AND OCTREOTIDE LABELED WITH $^{99m}$Tc, $^{188}$Re, AND $^{131}$I

The somatostatin-derived peptide analogues octreotide and RC-160 were evaluated in normal animals after direct labeling with $^{99m}$Tc and $^{188}$Re, and compared with the same peptides radiolabeled with $^{131}$I. The octreotide and RC-160 labeling kits were prepared and radiolabeled by the method of Example 2. The radioiodinations were performed using chloramine T by mixing 10 μg of peptide in 70 μl PBS with 10 μg chloramine T in 20 μl PBS and 10 μl of $^{131}$I or $^{125}$I solution. The iodinated peptide was applied to a $C_{18}$ minicolumn and the unbound iodine removed by elution with water. The iodinated peptide was eluted with methanol and dried under vacuum with a rotary evaporator. The dried material was dissolved in water containing 30% ethanol for RC-160 or phosphate buffered saline for octreotide. For in vivo use, the radiolabeled peptide was diluted 1:1 with pre-filtered 20% human serum albumin. This solution of peptide in albumin showed no signs of precipitation even upon cooling and overnight storage at 4° C.

Dynamic Imaging Studies. Dynamic imaging studies were performed in adult, male Wistar rats. The animals were anesthetized using an intraperitoneal injection of typically 0.6 ml of ketamine/Rompun (1.4:0.2; v:v). For the $^{99m}$Tc and $^{188}$Re studies, the animals were placed in a supine position on the head of a medium energy, high resolution planar gamma camera. For the $^{131}$I studies, the animals were placed on the head of a high energy planar gamma camera. The animals were injected in the tail vein with 0.1–0.2 ml of test material. Images were collected in 30 second intervals for the first 2 minutes, and after that in 2 minute intervals for 30 minutes. In some cases static images (10 minute collection) were performed for periods up to 2 hours post-injection. Region-of-interest (RIO) methods were used to evaluate the amount of radioactivity in the whole animal and in selected organs over time. Dynamic imaging study of $^{99m}$Tc-RC-160 in an adult male rat revealed rapid clearance to the liver and after 10 minutes uptake to the stomach. No other organ appeared to be involved in uptake or clearance. Thyroid uptake was not noted nor was more than a slight uptake in the kidneys and bladder observed. Dissection of the animal post-study confirmed uptake to the stomach. The majority of the activity was in the stomach contents. Most of the activity in the stomach tissue was found in the posterior portion of the stomach. Region-of-interest evaluation of the heart/lung as representative of blood pool indicated a biphasic blood clearance. By 30 minutes post-injection blood clearance was clearly in the secondary portion of the clearance curve. This was in contrast to the clearance of $^{99m}$Tc-octreotide which cleared to the liver/intestine primarily, but also to the kidney/bladder.

Dynamic imaging of $^{131}$I-RC-160 also revealed a rapid clearance to the liver and then clearance to the stomach. The overall pattern of clearance was essentially identical to that observed for $^{99m}$Tc-RC-160. Dynamic imaging of $^{188}$Re-RC-160 revealed a rapid clearance to the liver, however, unlike the $^{99m}$Tc-and $^{131}$I-labeled RC-160, it was cleared into the intestine. A repeat imaging after 24 hours revealed very little residual activity and no accumulation in bone or other tissue. By 30 minutes most of the radioactivity had cleared from the blood and the liver, and could be found in the small intestine. This overall pattern of clearance was essentially identical to $^{181}$Re-octreotide which also cleared to the liver.

Biodistribution Studies in Mice. Biodistribution studies were performed in adult, female NMRI mice (approximately 25 g) at selected times (15 and 120 minutes) after injection into the tail vein. Each experimental group was composed of at least five animals, with each animal receiving 0.2 ml containing approximately 4 μCi. Animals were sacrificed by ether overdose, and selected organs dissected, weighed, and associated radioactivity determined. Data were analyzed using a computer program specifically designed for $^{99m}$Tc-labeled preparations. The percent dose per organ for blood, bone, and muscle were calculated assuming 7, 8.2, and 40% of total body weight, respectively, for these tissues. In some of the studies, the results were standardized to a total body weight of 30 g. The general observations obtained by dynamic imaging were used to select time points for comparative biodistribution studies. The biodistributions of the various radiolabeled peptide preparations were evaluated in normal mice at 15 minutes and 120 minutes after injection. The results were substantiated by dynamic imaging techniques in normal rats. $^{99m}$Tc-RC-160 cleared rapidly from the blood to the liver and subsequently the intestines. No other organ appeared to be significantly involved in uptake or clearance with the exception of the stomach. This was in contrast to the clearance of $^{99m}$Tc-octreotide which cleared to the liver and subsequently the intestines, but also to the kidneys. $^{99m}$Tc-RC-160 cleared faster from the blood than $^{99m}$Tc-octreotide. The biodistributions of $^{188}$Re-octreotide and $^{188}$Re-RC-160 were much more similar to each other than that of their $^{99m}$Tc-labeled counterparts with significant clearance to the liver and subsequently to the intestines and low accumulation in the kidneys. The renal uptake of $^{188}$Re-octreotide was significantly higher than that of $^{188}$Re-RC-160. Both $^{188}$Re-labeled analogues showed higher amounts of radioactivity associated with the blood at both 15 minutes and 120 minutes post-injection (when compared to the $^{99m}$Tc-analogues), although $^{188}$Re-RC-160 cleared slower than $^{188}$Re-octreotide.

EXAMPLE 7—INTRATHORACIC RADIOTHERAPY OF HUMAN SMALL-CELL LUNG CARCINOMA IN NUDE MICE WITH $^{188}$Re-RC-160

The therapeutic efficacy of $^{188}$Re-RC-160 in experimental models of human small cell lung carcinomas which mimic the clinical presentation was evaluated. In the experimental model, cells from the human small cell lung carcinoma cell line NCI-H69 cells were inoculated into the thoracic cavity of athymic mice and rats. Subsequently, the biodistribution of $^{188}$Re-RC-160 was monitored as was the effect on the subsequent growth of tumors. The cell line NCI-H69 was derived from a human small cell lung carcinoma and has been used in concert with experimental, therapeutic radiopharmaceutical. In nude mice NCI-H69 tumors exhibit reduced tumor volumes when treated intra-lesionally with unlabeled somatostatin analogues, including RC-160 (Pinski J, Schally A V, Halmos G, Szepenazi K, Groot K, O'Byme K, Cai R Z: Effects of somatostatin analogue RC-160 and bombesin/gastrin-releasing peptide antagonists on the growth of human small-cell and non-small-cell lung carcinomas in nude mice, *Br J Cancer* 70: 886–892, 1994). The cell line produces tumors when implanted subcutaneously or introduced into the thoracic cavity or lung parenchyma.

Peptide Labeling. RC-160 was synthesized by classical synthesis and supplied by DeBiopharm S. A. (Lausanne, Switzerland), with RC-160 radiolabeling kits prepared in 6 ml capacity amber vials and containing a final volume of 2.0 ml. Each kit contained 500 μg peptide in tartrate/phthalate buffer, pH 5.2, containing stannous tartrate to reduce the perrhenate, together with excipients. All kits were prepared using nitrogen purged solutions and the head space gas was similarly purged with nitrogen gas. Vials were stored frozen at −30° C. For labeling, 2.0 ml of a $^{188}$Re-perrhenate solution (15–20 mCi) was added (final labeling volume 4 ml), and the vial heated at 80° C.–90° C. for 30 minutes with periodic mixing. At the end of the incubation period, the solution was allowed to cool slightly and an aliquot removed for radiochemical analysis. Prior to use in animals, aliquots were mixed 1:1 with 20% human serum albumin (clinical-grade).

Biodistributon Studies. Biodistribution studies were performed in adult, female nu/nu mice at selected times after injection into the pleural cavity. Each experimental group was composed of at least five animals, with each animal receiving 0.1 ml containing approximately 4 μCi. Animals were sacrificed by ether overdose, and selected organs dissected, weighed, and associated radioactivity determined. The data was calculated as the percentage dose per gram of tissue, although in some cases the data was also calculated as the percentage dose per organ. After 4 hours significant accumulations of radioactivity were found associated with the lungs, heart, intestines, and chest wall. A 1 ml wash of the thoracic cavity (prior to organ removal) recovered nearly 5% of the total injected dose. Lesser amounts of radioactivity were associated with the liver and kidneys. After 24 hours, the lung retained the highest percentage of the injected dose/gram, although significant accumulations were found associated with the chest wall, heart, and in a wash of the thoracic cavity. A comparison was made of the amount of $^{188}$Re-RC-160 associated with the thoracic cavity in animals which had been inoculated with NCI-H69 cells in the thoracic cavity compared to that found in animals which received no tumor cells. Tumored animals had a markedly higher retention, especially after 24 hours.

Effects on Tumors. In these studies animals were inoculated with 5–7.5×10$^6$ NCI-H69 cells in 0.1 ml of serum-free RPMI medium. The cells were introduced by injection with a 26 gauge needle from a position ventral and midline over the liver and under the rib-cage. The test materials (RC-160 and $^{188}$Re-RC-160) were similarly injected into the pleural cavity with a 26 gauge needle from a position ventral and midline over the liver and under the rib-cage. Each injection contained approximately 5 μg of peptide in a volume of 0.1 ml and a radioactive dose (when used) of 200 μCi. In an initial study, the animals were: a) treated on 1 day and 5 days with 200 μCi doses of $^{188}$Re-RC-160, or b) received no treatment. After 28 days the animals were euthanized and the thoracic cavity examined. In the group treated with $^{188}$Re-RC-160, no evidence of tumors was found in 8/10 animals, while 2/10 animals had minimal disease. In the group with no treatment, 7/7 exhibited local disease restricted to the thoracic cavity. In all cases the visible tumor burdens were low. No alterations in overall lung morphology were observed in "normal" animals administered similar dose regimens of $^{188}$Re-RC-160.

In a second study, the animals were: a) treated with $^{188}$Re-RC-160 on days 14, 17, and 25, b) treated with RC-160 alone (on the same days and with the same amount of peptide), or c) left with no treatment. Results are shown in the following table:

TABLE 1

Effect of intra-thoracic treatment of athymic mice initiated two weeks after inoculation in the thoracic cavity of 5.0 × 10$^6$ NCI-H69 small cell lung carcinoma cells. Each "X" marks the response from an individual animal and "—" indicates that no animal was observed to exhibit this response.

|  | $^{188}$Re-RC-160 | RC-160 | None |
|---|---|---|---|
| No Evidence of Tumor | XXXXXX | — | — |
| Minimal Tumor Burden | XXX | X | X |
| Confined Tumor Burden | X | XXXX | XXXX XX |
| Extended Tumor Burden | — | XXX | XXX |

Animals treated with RC-160 and $^{188}$Re-RC-160 exhibited an initial loss of weight following treatments. This loss of weight appears to resolve with time. In the animal group treated with $^{188}$Re-RC-160, no evidence of tumor or minimal tumor burdens were found in 5/5 animals at 48 days after initial inoculation with tumor cells. On the other hand, 3/3 of the animals treated with only RC-160 had tumors and 5/5 of the animals which received no treatment had tumors. In these studies, an anti-tumor response was observed using $^{188}$Re-RC-160 administered into the pleural cavity. Comparison with results using RC-160 demonstrates that the therapeutic response is due to the $^{188}$Re-RC-160, and not to just the peptide alone. Transient weight loss was the only visible evidence of treatment.

EXAMPLE 8—LONG-TERM ANIMAL THERAPY TRIALS WITH RHENIUM-LABELED SOMATOSTATIN-DERIVED PEPTIDE

A series of experiments were conducted, comparing $^{188}$Re-RC-160 prepared by the method of Example 3, and labeled by the method of Example 4, with a variety of preparations, and also conducting survival studies of nude mice with implanted human tumor xenografts. For these studies, PC-3 tumors in athymic mice were used, with treatment initiated when the tumors had a volume of 0.1 to 0.2 cm$^3$.

Initial Study. The initial study evaluated treatment of nude mice implanted with PC-3 human prostate tumors with $^{188}$Re-RC-160. 19 days after the tumor cells were implanted, treatment was started. Three groups of animals of 10 animals each were studied: 1) $^{188}$Re-RC-160 at 200 μCi in 0.2 ml injected intra-tumor on Fri, Mon, Wed, Fri, Mon, Wed, Fri, (7 doses); 2) sham injection, containing same volume and composition, but without $^{188}$Re-RC-160; and, 3) controls receiving no injections. Tumors were measured 3 times per week for 65 days and then once a week thereafter, and the animals were weighed once a week. Survival was recorded until day 109 when the experiment was terminated. At this time, all the sham-treated animals were dead.

The growth curves are shown in FIG. 1. In the treated group, all of the tumors stopped growing and shrunk to the size they were before treatment was started. Because the tumor cells were co-injected with Matrigel, a residual fibrous pad remained even if the tumor was dead. In contrast, all of the animals in both the sham group and the negative control group continued to grow. The sham-treated animals showed the greatest tumor size. In some of the treated animals tumors began to grow again at about 10 days post treatment. By 20 days post-treatment regime, the regrowing tumors were obviously larger and different in appearance. Growing tumors were colored, vascularized and stretching the skin. Dead or dormant tumors were white, avascular, and show no change in appearance over time. Apparent dead or dormant tumors which did not start to regrow in ten days remained unchanged until the end of the experiment.

Figure 2:
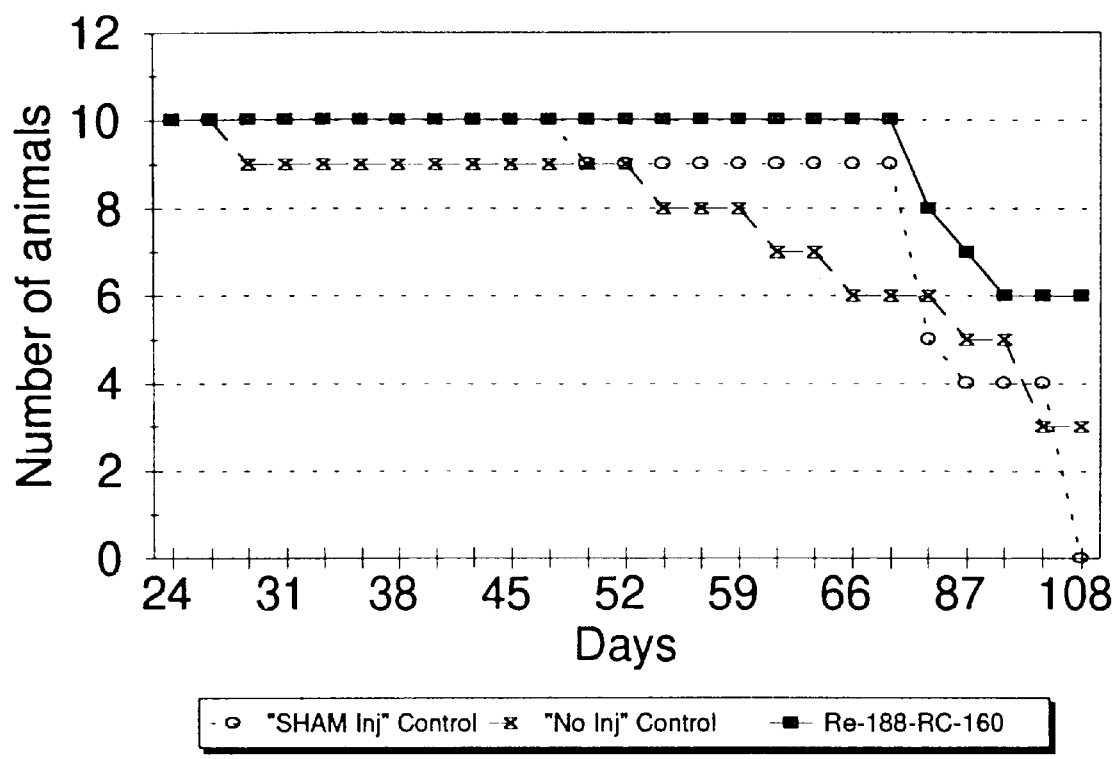
FIG. 2 shows the survival time, in days, for animals treated as described in FIG. 1.

In the treated group, 3 animals (30%) were cured, defined as no tumor growth at two months after the end of the treatment. 3 other animals in the treatment group showed regrowth of their tumors starting at about 10 days post treatment. At the termination of the experiment, all the sham injected animals had died. In most cases the tumors were as large in bulk as the rest of the animal's body. Some animals also experienced metastatic disease. Three of the non-treated animals remained alive, two with very bulky tumors indicating that they would die soon and one with a smaller tumor which was more slow growing. Six animals in the treated group were alive, three with growing tumors and three without tumor regrowth. See FIG. 2.

Figure 3:
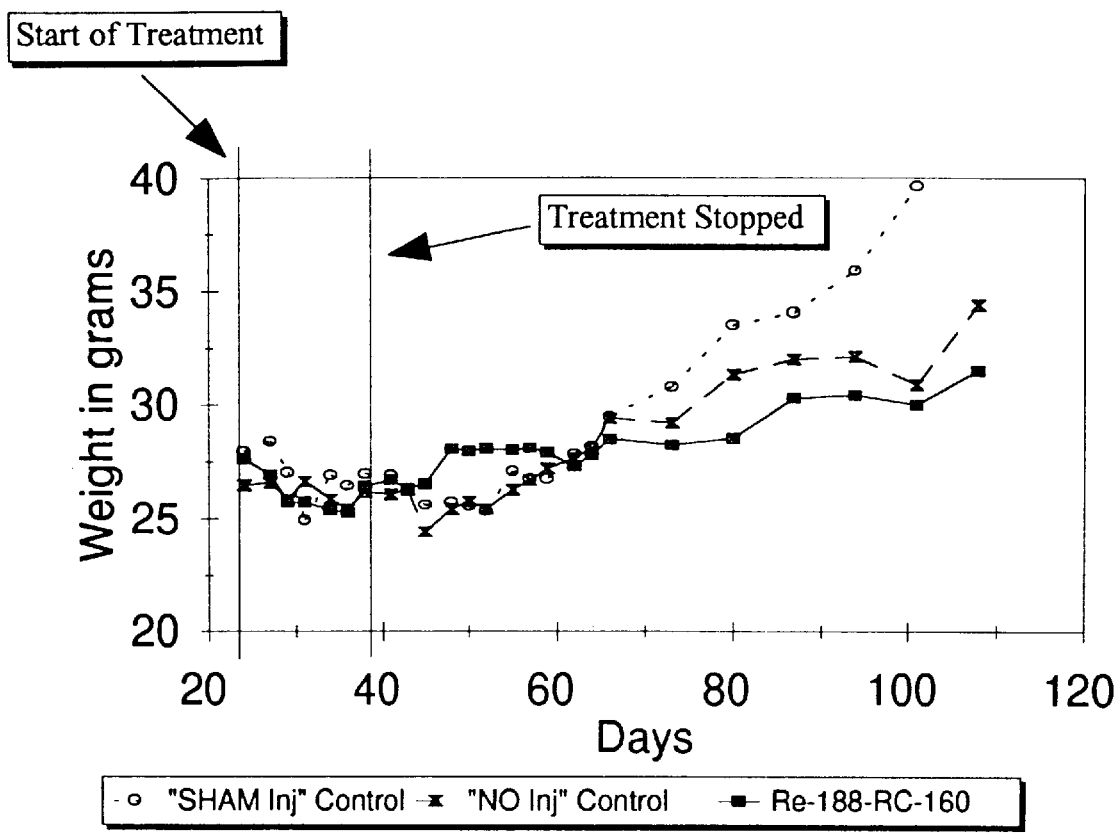
FIG. 3 shows the average body weight of animals treated as described in FIG. 1.

FIG. 3 shows the average body weights of the three groups of animals. The treated animals lost an average of about 6 grams of body weight, or about 20%. They recovered their original body weights in about 2 weeks after the treatment. This weight loss was associated with a decrease in food consumption during the treatment period. At the end of the experiment the surviving treatment group was about 120% heavier, on the average, than the untreated survivors. Weight loss and appetite loss were the only observed adverse effects except that one animal in the treatment group showed some swelling around the periphery of the tumor and another animal in the treatment group showed some radiation burn to the skin. Both of these animals had tumors which did not regrow and were healthy at the end of the experiment. Treatment of nude mice with growing implants of human prostate tumor, PC-3, was successful with a series of 7 injections of 200 μCi each of $^{188}$Re-RC-160. All animals had tumor regression, yielding a therapeutic response rate of 100%. Regrowth of tumors occurred in 7 of the treated animals beginning at about 10 days post treatment. 30% remained tumor-free for two months post-therapy.

Comparative Study. Since regrowth following tumor regression was observed in 70% of the animals using a series of 7 treatments of 200 μCi given every other day, a modified treatment plan was adopted. In this plan, a treatment schedule was used in which a series of doses were given over 5 sequential days, followed by a two week waiting period, and then a second series of doses for 5 days. In this experiment, nude mice with PC-3 tumor implants were treated with $^{188}$Re-RC-160, in comparison to animals treated with RC-160, $^{188}$Re-IKVAV (SEQ. ID NO. 1), a peptide which also binds to prostate cancer, and no injection controls. PC-3 tumors were implanted into a series of 40 nude mice, yielding four groups of ten animals. When the tumors became well enough established to begin the treatment, the animals were treated daily for one week. After a two week recovery period, one-half of the animals in each of the previous 4 groups were again treated daily as shown below.

| | Treatment Design | |
|---|---|---|
| Group | First Treatment | Second Treatment |
| 1a | no injection control | none |
| 1b | no injection control | $^{188}$Re-RC-160 |
| 2a | RC-160 | none |
| 2b | RC-160 | $^{188}$Re-RC-160 |
| 3a | $^{188}$Re-IKVAV (SEQ. ID NO. 1) | none |
| 3b | $^{188}$Re-IKVAV (SEQ. ID NO. 1) | $^{188}$Re-RC-160 |
| 4a | $^{188}$Re-RC-160 | none |
| 4b | $^{188}$Re-RC-160 | $^{188}$Re-RC-160 |

Using this protocol, tumors were more effectively treated than in the prior experiment, since the cure rate went from 30% to 80% in the group receiving the two serial treatments. However, the group which received only the second treatment also revealed an 80% cure rate. Treating with RC-160 alone failed to produce any cures, as did treating with $^{188}$Re-IKVAV (SEQ. ID NO. 1), suggesting that it is the combination of the RC-160 with the $^{188}$Re which yields the biological effect.

| | Treatment Results | |
|---|---|---|
| First Treatment | Second Treatment | Percent Cured (No Regrowth After 4 Weeks) |
| no injection control | none | 0% |
| no injection control | $^{188}$Re-RC-160 | 80% |
| RC-160 | none | 0% |
| RC-160 | $^{188}$Re-RC-160 | 40% |
| $^{188}$Re-IKVAV (SEQ. ID NO. 1) | none | 0% |
| $^{188}$Re-IKVAV (SEQ. ID NO. 1) | $^{188}$Re-RC-160 | 40% |
| $^{188}$Re-RC-160 | none | 0% |
| $^{188}$Re-RC-160 | $^{188}$Re-RC-160 | 80% |

Tumor growth was significantly reduced by the first treatment. Although the difference was not statistically significant, it was surprising to observe that the RC-160 tumors appeared to grow faster than the controls. The observation was that RC-160, while it is being administered, slows or regresses tumor growth. But when these tumors start to regrow, they seem to grow faster than the controls, as shown below:

Tumor Size Two Weeks after the First Treatment

| Group | Average tumor volume, cm³ | p-value |
|---|---|---|
| RC-160 | 0.556 | 0.0010 |
| no injection control | 0.419 | 0.0224 |
| $^{188}$Re-IKVAV (SEQ. ID NO. 1) | 0.315 | 0.14 |
| $^{188}$Re-RC-160 | 0.120 | |

In order to better understand the treatment effects, individual tumor growth curves were analyzed. Without treatment, tumor size continued to increase. After about 25 days the tumors of three animals began to grow at accelerated rates while others continued to grow at about the same rate. The animals lose weight during the treatment. They are observed to not eat much during this period. Their weights return to normal following treatment, and then the animals continue to grow. In controls, the animal weight measurements become misleading as the tumors grow large. In some instances the animals are obviously losing weight as their tumors become as large as they are. The measured body weights are the sum of growing tumor and the shrinking body. The phenomenon of accelerated tumor growth starting about three weeks after beginning of the experiment was also observed in some of the animals treated with RC-160 alone. This was also observed in some animals receiving the $^{188}$Re-IKVAV (SEQ. ID NO. 1), but was delayed by 1 to 3 weeks.

Figure 4:
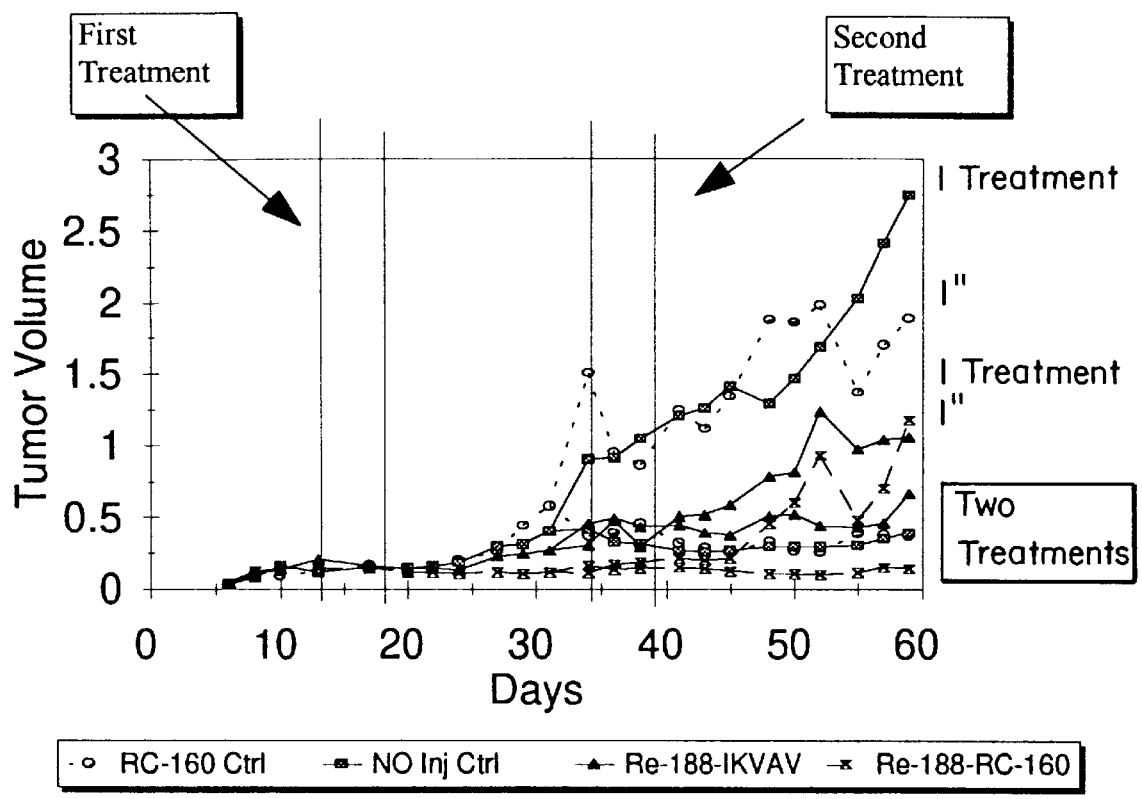
FIG. 4 shows data from a comparative study of tumor growth in cm$^3$ for animals treated over 5 sequential days, followed by a two week waiting period, and then a second series of doses for 5 days. In this experiment, nude mice with PC-3 tumor implants were treated with $^{188}$Re-RC-160, in comparison to animals treated with RC-160, $^{188}$Re-IKVAV (SEQ. ID NO. 1), a peptide which also binds to prostate cancer, and no injection controls. There were 10 animals in each initial growth; at the time of the second treatment, the animals in each group were subdivided into two sub-groups, with one sub-group receiving no treatment, and the second sub-group receiving $^{188}$Re-RC-160. Thus, each group bifurcates on commencement of the second treatment. The lower 4 lines at the right terminus of the Y-axis all represent sub-groups receiving a second treatment of $^{188}$Re-RC-160.
Figure 5:
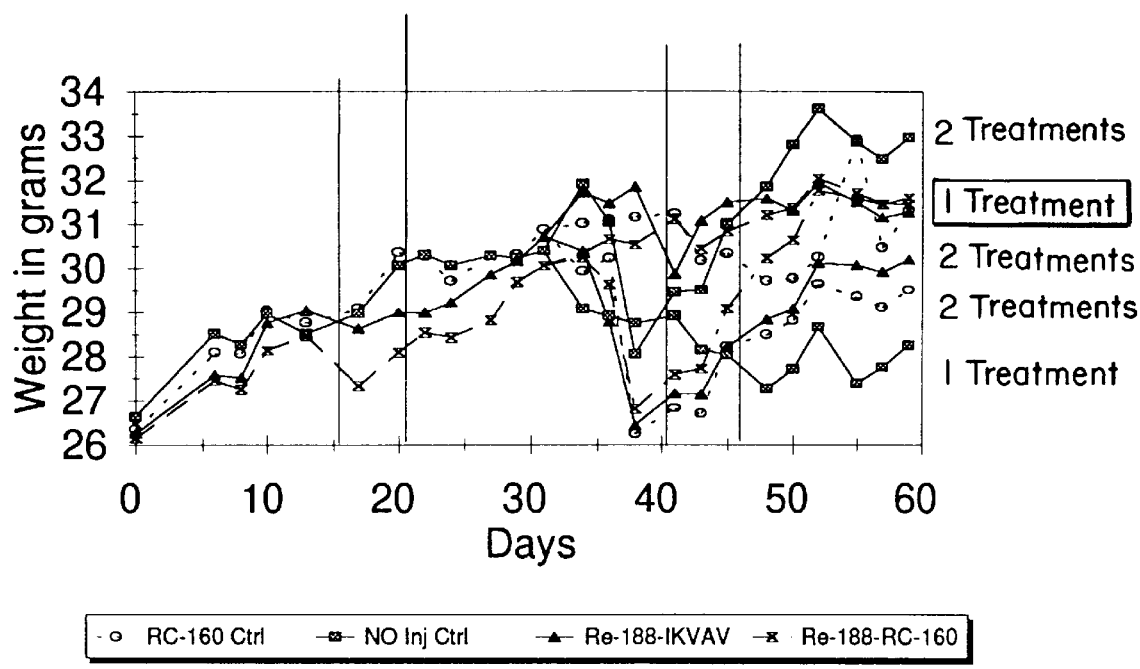
FIG. 5 shows average body weights for the groups and sub-groups described in FIG. 4.

The $^{188}$Re-RC-160 caused some loss of body weight during treatment, which was recovered over the following 3 weeks. See FIG. 4 and FIG. 5. When animals were treated a second time the drop in body weight was more dramatic. However, recovery is rapid, about 2 weeks. $^{188}$Re-IKVAV (SEQ. ID NO. 1) treatment also caused a drop in weight during treatment.

$^{188}$Re-RC-160 is highly effective in reducing tumors in animals receiving direct injections of the material into their tumors. In all cases the tumors of $^{188}$Re-RC-160 treated animals decreased in size, and 80% did not regrow when given two serial treatments. These animals were apparently cured of their cancers. $^{188}$Re-RC-160 was more effective that either RC-160 alone or $^{188}$Re coupled to a different peptide.

Figure 6:
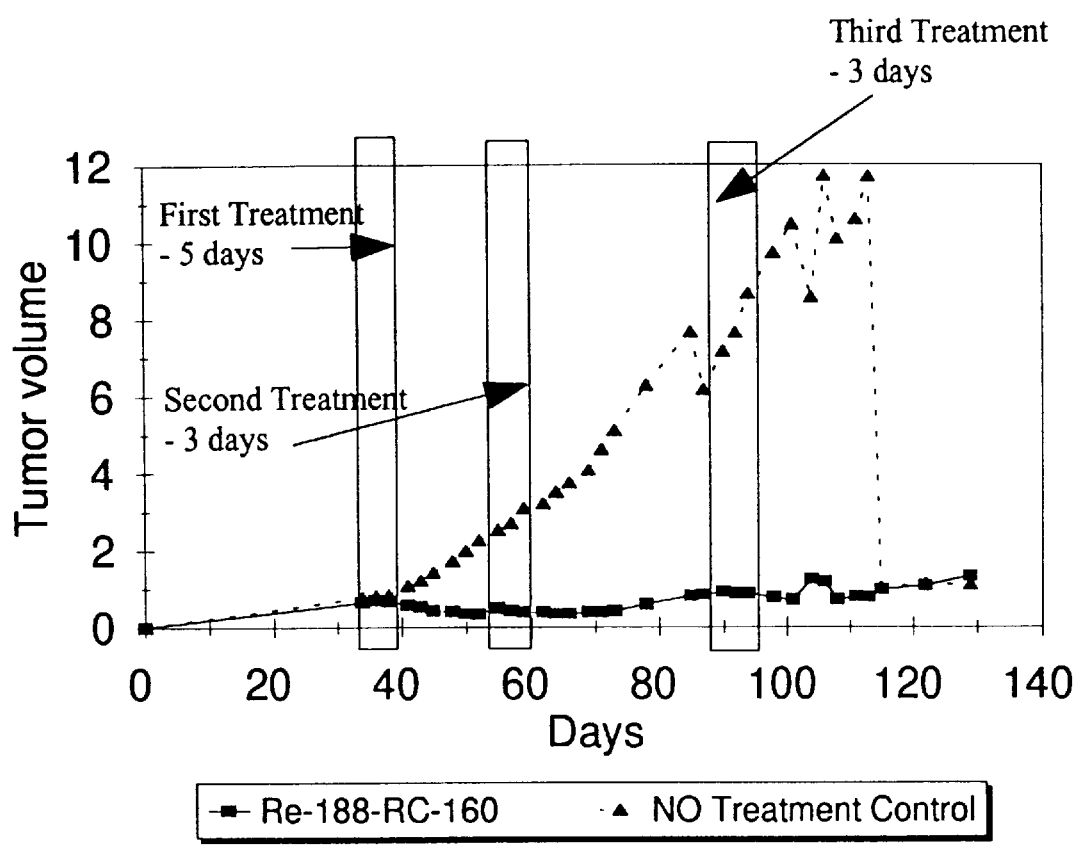
FIG. 6 shows data from a three treatment regime, in which animals with PC-3 tumor xenografts were divided into two groups, one receiving three series of $^{188}$Re-RC-160, and the other receiving no treatment. This figure shows shows average tumor volume, in cm$^3$. By day 120, only one animal remained in the "No treatment control" group, and it had a relatively light tumor burden, giving rise to a precipitous drop in tumor volume.
Figure 7:
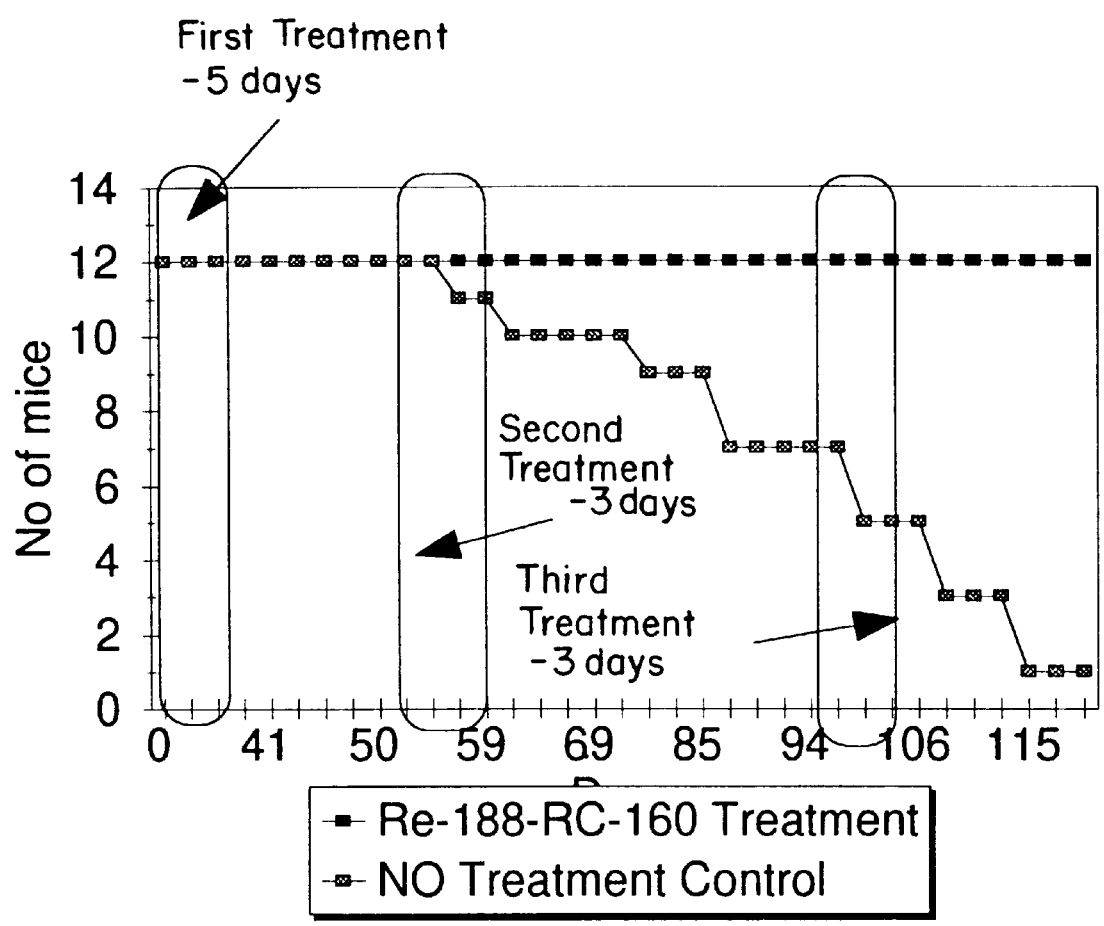
FIG. 7 shows actual survival time, in days, for the animals treated as described for FIG. 6.

Three Treatment Regime. An additional experiment was conducted, comparing two groups of twelve mice each, with PC-3 tumor xenograft implants. One group received no treatment, and served as a control. The other group received $^{188}$Re-RC-160, given as a direct intra-tumor injection, with three treatment series; the first treatment was for five consecutive days followed by no treatment for 17 days, a second series of treatment for three consecutive days followed by no treatment for 31 days, and concluding with a third series of treatment for three consecutive days. FIG. 7 shows tumor growth; the animals receiving no treatment exhibited continual tumor growth, while the treated animals showed regression in tumor volume following treatment. As is shown in FIG. 6, all animals receiving $^{188}$Re-RC-160 survived through 120 days post-initiation of the experiment. All but one animal in the no treatment control had died by that date.

$^{186}$Re and $^{188}$Re Compared. In another study, using of RC-160 labeled with reactor produced $^{186}$Re was compared to generator produced $^{188}$Re. All animals had PC-3 tumor xenografts as described above, and were treated with equal μCi amounts of either $^{188}$Re-RC-160 or $^{186}$Re-RC-160, with animals receiving no treatment serving as controls. Tumor regression was observed with both $^{188}$Re-RC-160 and $^{186}$Re-RC-160.

EXAMPLE 9—THERAPY OF HUMAN GLIOBLASTOMA MULTIFORME BY REGIONAL ADMINISTRATION OF RHENIUM-LABELED SOMATOSTATIN-DERIVED PEPTIDE

Either octreotide, RC-160 somatostatin-derived peptide analogue, or other somatostatin-derived peptide analogues are labeled with either $^{188}$Re or $^{186}$Re by the methods of Examples 2, 3 or 4. Patients with glioblastoma multiforme have the rhenium-labeled, somatostatin-derived peptide directly injected into the tumor site, using ultrasound, CT scanning or other imaging modalities to localize the cancer within the brain. Repeated doses are given as necessary. Localization of the agent, dosimetry, and other parameters may be determined by gamma camera evaluation, or similar means, utilizing the gamma of $^{188}$Re or $^{186}$Re. Optionally, prior to administration of the rhenium-labeled therapeutic dose, efficacy of therapy may be predicted by administration of an imaging dose, using either an indium or technetium label, to determine whether sufficient somatostatin receptors are present on the tumor. Such imaging dose may be the same somatostatin-derived peptide analogue as will be used for therapy, or may be another analogue which is demonstrated to bind to the same somatostatin receptor. For $^{99m}$Tc labeled peptides, such may be labeled by the methods of Examples 1, 2, 3 or 4. Alternatively, commercially available products such as $^{111}$In-DTPA-octreotide may be employed.

EXAMPLE 10—THERAPY OF HUMAN PROSTATE CANCER BY REGIONAL ADMINISTRATION OF RHENIUM-LABELED SOMATOSTATIN-DERIVED PEPTIDE

Either octreotide, RC-160 somatostatin-derived peptide analogue, or other somatostatin-derived peptide analogues are labeled with either $^{188}$Re or $^{186}$Re by the methods of Examples 2, 3 or 4. Patients with localized prostate cancer have the rhenium-labeled, somatostatin-derived peptide directly injected into the tumor site, optionally using ultrasound, CT scanning or other imaging modalities to localize the cancer within the prostate. Repeated doses are given as necessary. Localization of the agent, dosimetry, and other parameters may be determined by gamma camera evaluation, or similar means, utilizing the gamma of $^{188}$Re or $^{186}$Re. In the alternative, such agents may be regionally injected within the prostate fascia following surgery, either as a prophylactic measure, or in response to evidence of disease recurrence, such as an increase in prostate specific antigen (PSA) levels. Optionally, prior to administration of the rhenium-labeled therapeutic dose, efficacy of therapy may be predicted by administration of an imaging dose, using either an indium or technetium label, to determine whether sufficient somatostatin receptors are present on the tumor. Such imaging dose may be the same somatostatin-derived peptide analogue as will be used for therapy, or may be another analogue which is demonstrated to bind to the same somatostatin receptor. For $^{99m}$Tc labeled peptides, such may be labeled by the methods of Examples 1, 2, 3 or 4. Alternatively, commercially available products such as $^{111}$In-DTPA-octreotide may be employed.

EXAMPLE 11—THERAPY OF HUMAN PANCREATIC CANCER BY REGIONAL ADMINISTRATION OF RHENIUM-LABELED SOMATOSTATIN-DERIVED PEPTIDE

Either octreotide, RC-160 somatostatin-derived peptide analogue, or other somatostatin-derived peptide analogues are labeled with either $^{188}$Re or $^{186}$Re by the methods of Examples 2, 3 or 4. Patients with localized pancreatic cancer have the rhenium-labeled, somatostatin-derived peptide directly injected into the tumor site, optionally using ultrasound, CT scanning or other imaging modalities to localize the cancer within the pancreas. Repeated doses are given as necessary. Localization of the agent, dosimetry, and other parameters may be determined by gamma camera evaluation, or similar means, utilizing the gamma of $^{188}$Re or $^{186}$Re. Optionally, prior to administration of the rhenium-labeled therapeutic dose, efficacy of therapy may be predicted by administration of an imaging dose, using either an indium or technetium label, to determine whether sufficient somatostatin receptors are present on the tumor. Such imaging dose may be the same somatostatin-derived peptide analogue as will be used for therapy, or may be another analogue which is demonstrated to bind to the same somatostatin receptor. For $^{99m}$Tc labeled peptides, such may be labeled by the methods of Examples 1, 2, 3 or 4. Alternatively, commercially available products such as $^{111}$In-DTPA-octreotide may be employed.

EXAMPLE 12—THERAPY OF CANCERS WITHIN THE PLEURAL CAVITY BY REGIONAL ADMINISTRATION OF RHENIUM-LABELED SOMATOSTATIN-DERIVED PEPTIDE

Either octreotide, RC-160 somatostatin-derived peptide analogue, or other somatostatin-derived peptide analogues are labeled with either $^{188}$Re or $^{186}$Re by the methods of Examples 2, 3 or 4. Patients with cancers within the pleural cavity have the rhenium-labeled, somatostatin-derived peptide directly injected into the pleural cavity. Optionally, such peptide may also be injected directly into one or more tumors within the pleural cavity, using ultrasound, CT scanning or other imaging modalities to localize the cancer within the pleural cavity or lung. Repeated doses are given as necessary. Localization of the agent, dosimetry, and other parameters may be determined by gamma camera evaluation, or similar means, utilizing the gamma of $^{188}$Re or $^{186}$Re. Such cancers may be primary cancers within the pleural cavity, or may be metastatic tumors, secondary to small cell lung carcinoma, breast cancer, ovarian cancer or other cancers. Optionally, prior to administration of the rhenium-labeled therapeutic dose, efficacy of therapy may be predicted by administration of an imaging dose, using either an indium or technetium label, to determine whether sufficient somatostatin receptors are present on the tumors within the pleural cavity. Such imaging dose may be the same somatostatin-derived peptide analogue as will be used for therapy, or may be another analogue which is demonstrated to bind to the same somatostatin receptor. For $^{99m}$Tc labeled peptides, such may be labeled by the methods of Examples 1, 2, 3 or 4. Alternatively, commercially available products such as $^{111}$In-DTPA-octreotide may be employed. The indium or technetium labeled imaging dose may be delivered systemically, such as by intravenous injection, or may be delivered regionally, such as by direct injection into the pleural cavity.

EXAMPLE 13—EFFECT OF CARRIER MOLECULES ON THE RETENTION AND BIODISTRIBUTION OF RHENIUM-LABELED SOMATOSTATIN-DERIVED PEPTIDE

Figure 8A:
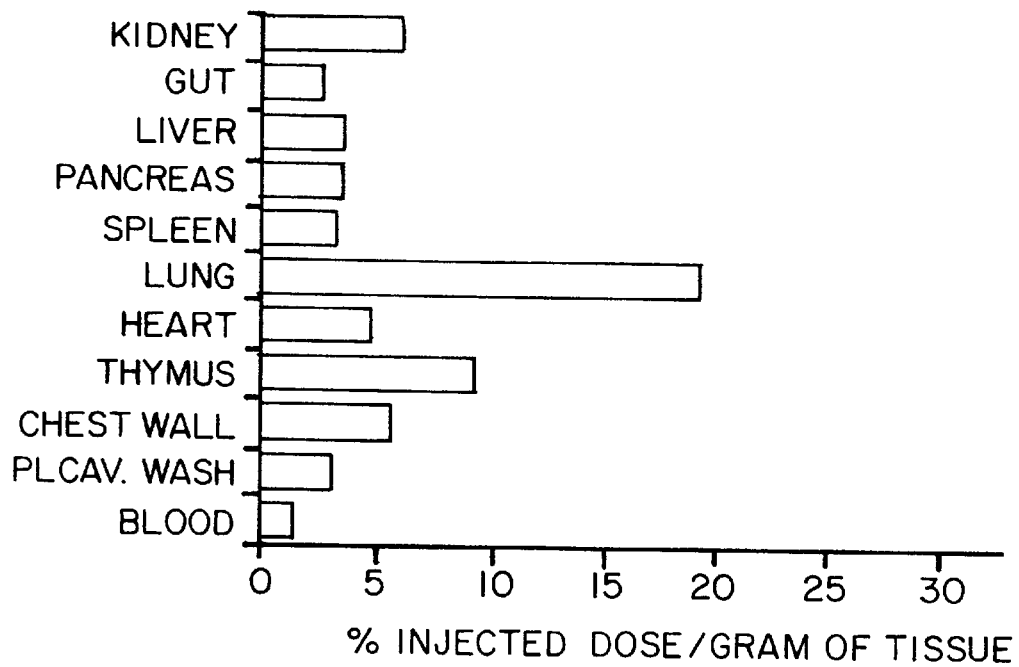
FIG. 8*a* and 8*b* shows retention and biodistribution, at 24 hours, of $^{188}$Re-RC-160 administered mixed with human serum albumin and mixed with human gamma globulin.
Figure 8B:
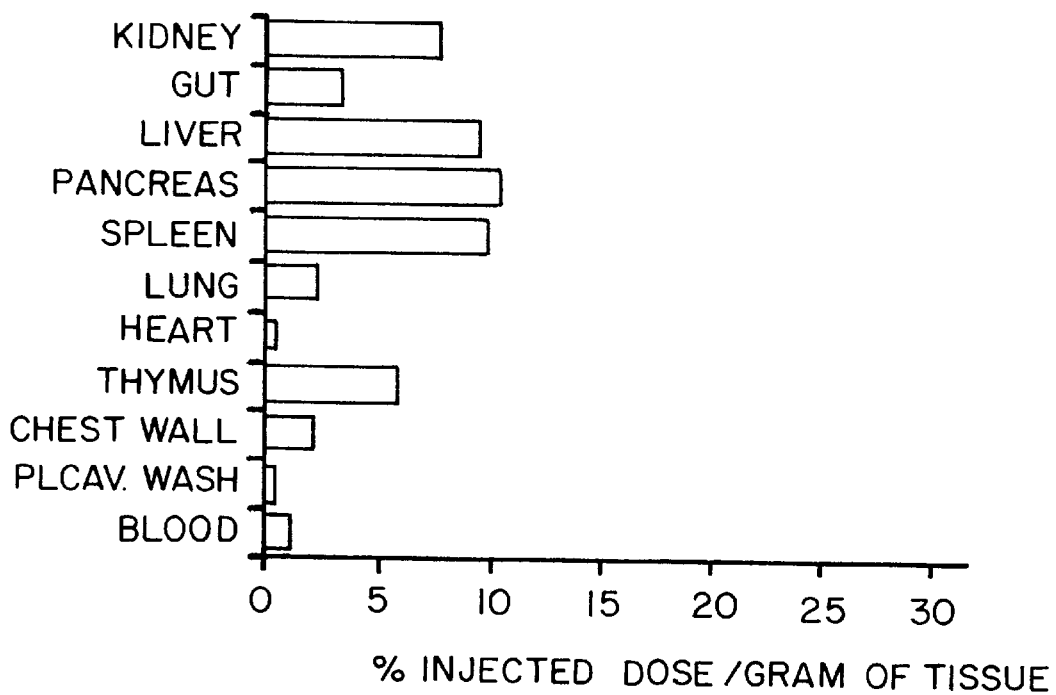

The effect on organ retention and biodistribution of co-administration with various carrier molecules was evaluated. Preliminary studies showed high binding of $^{188}$Re-RC-160 to serum proteins as determined by precipitation and microfiltration, on the order of 80%. Soluble $^{188}$Re-RC-160 was prepared by the method of Example 2, and was mixed with either 10% serum albumin, 10% human gamma globulin or 4% isotonic glucose. The preparation was injected into the pleural cavity of normal BALB/c female mice, and retention and biodistribution evaluated at 4 and 24 hours post injection. Significant differences were observed between the three preparations, with lung, thymus and plural cavity retention significantly increased by co-administration of soluble $^{188}$Re-RC-160 and human gamma globulin, as is shown on FIG. 8a and 8b. Similar results were obtained at the four hour timepoint. Generally speaking, co-administration with serum protein, and particularly human gamma globulin, increased retention of the $^{188}$Re-RC-160 in the region or cavity into which it was injected.

EXAMPLE 14—THERAPY OF CANCERS WITH RHENIUM-LABELED SOMATOSTATIN-DERIVED PEPTIDE CO-ADMINISTERED WITH A CARRIER MOLECULE

Either octreotide, RC-160 somatostatin-derived peptide analogue, or other somatostatin-derived peptide analogues are labeled with either $^{188}$Re or $^{186}$Re by the methods of Examples 2, 3 or 4. Such radiolabeled peptide is mixed with a carrier molecule, for example a serum protein such as human serum albumin or human gamma globulin, and the radiolabeled peptide co-administered with the carrier molecule. If injected directly into a tumor, the radiolabeled peptide exhibits increased retention within the tumor. If injected into a compartment, such as the pleural cavity, the radiolabeled peptide exhibits increased retention with the compartment.

EXAMPLE 15—THERAPY OF CANCERS USING PARTICULATE FORMS OF RHENIUM-LABELED SOMATOSTATIN-DERIVED PEPTIDE

RC-160 somatostatin-derived peptide analogue is labeled with either $^{188}$Re or $^{186}$Re by the method of Example 2 to result in a colloidal or particulate form of the radiolabeled preparation. Patients with cancers are treated with this rhenium-labeled RC-160. The preparation is injected directly into an artery feeding the tumor to be treated, where the particulates will lodge within the capillary bed of the tumor. Alternatively, the preparation is injected into a cavity containing the cancer, such as for treatment of tumors within the pleural cavity, in which case the rhenium-labeled, somatostatin-derived peptide particulate is directly injected into the pleural cavity. Alternatively, such peptide particulate may also be injected directly into one or more tumors, optionally using ultrasound, CT scanning or other imaging modalities to localize the cancer. Repeated doses are given as necessary. Localization of the agent, dosimetry, and other parameters may be determined by gamma camera evaluation, or similar means, utilizing the gamma of $^{188}$Re or $^{186}$Re.

EXAMPLE 16—THERAPY OF RHEUMATOID ARTHRITIS BY INTRA-ARTICULAR ADMINISTRATION OF A RHENIUM-LABELED SOMATOSTATIN-DERIVED PEPTIDE

RC-160 somatostatin-derived peptide analogue is labeled with either $^{188}$Re or $^{186}$Re by by any method described here or elsewhere, and specifically by the method of Example 2 but with radiolabeling at pH 6 or greater, to result in a colloidal form of the radiolabeled preparation. Patients with rheumatoid arthritis are treated with this rhenium-labeled RC-160. The use of $^{188}$Re-RC-160 as a radiopharmaceutical is particularly applicable to joint therapy of the knee, ankle, hip, shoulder, elbow, wrist, and phalanges, with applied radiation doses dependent on the size of the joint, but generally below 10 mCi. The preparation is injected directly into a large joint known to be the site of an arthritic inflammation, where the colloid will lodge within the joint and surrounding bone structures. Repeated doses are given as necessary. Localization of the agent, dosimetry, and other parameters may be determined by gamma camera evaluation, or similar means, utilizing the radiation of $^{188}$Re or $^{186}$Re.

EXAMPLE 17—PREPARATION OF A STABILIZED RHENIUM-LABELED RC-160 PEPTIDE-BASED RADIOPHARMACEUTICAL COMPOSITION

RC-160 radiolabeling kits were prepared using aseptic techniques. Each kit was prepared in a 10 ml serum vial using a 2 ml liquid fill. The liquid fill contained 200 μg of RC-160 peptide in 45 mM sodium potassium tartrate, 10 mM potassium hydrogen phthalate buffer, pH 5.0, in 5 mM stannous tartrate with 1% maltose added as a freeze-drying excipient. Each kit contained a maximum of 1.19 μg of tin. After filling, the vials were lyophilized, the head space gas filled with nitrogen, and the vials stoppered and crimped. Lyophilized vials were then stored refrigerated at 2–8° C. To label a kit, 4–5 ml of $^{188}$Re-perrhenate solution containing 10–100 mCi was added to the kits, and the kits then heated in a boiling water bath for 30–45 minutes. Following a brief cooling period, 2 ml of Ascorbic Acid for Injection, USP was added to the labeled kit through a 0.22 micron filter. Two types of parenteral ascorbate were used with similar results, Ascorbic Acid for Injection, USP, 500 mg/2 ml and Ascorvit 100 mg (Jenapharm, Germany).

$^{188}$Re-RC-160 to which ascorbate was not added was found to be stable for up to two hours post-labeling; however, after that the $^{188}$Re-RC-160 began to undergo an uncoupling from the peptide as determined by ITLC and confirmed by HPLC. This uncoupling occurred with $^{188}$Re, but not with Tc-99m when used in the same amounts, 20 mCi, suggesting the effect was specific to rhenium.

Post-labeling addition of ascorbate was found to essentially eliminate the uncoupling and stabilize the $^{188}$Re-RC-160. An HPLC profile at 30 hours post-labeling with 65 mCi to which ascorbate was added after labeling, demonstrated that very little free rhenium could be found. Cysteine displacement studies with ascorbate-stabilized Re-RC-160 demonstrated that the Re/peptide bond strength was not altered by use of the ascorbate, with the EC$_{50}$ for the ascorbate-stabilized material similar to that obtained without the use of ascorbate.

Addition of sodium sulfite (1 mg/ml pH 7.4), sodium bisulfite (1 mg/ml, pH 5.5), or mixtures of ascorbate and sodium sulfite (Ascorvit™ formulation), sodium bisulfite, or EDTA (Ascorbate for Injection, USP, formulation) were also effective in stabilizing the Re-RC-160, although not as effectively as using ascorbate alone. The addition of 50 mg/ml ascorbate yielded the same results as adding 250 mg/ml of ascorbate. The addition of ascorbate to $^{188}$Re-RC-160 labeled at 37° C. did not result in an improved labeling efficiency or substantial change in the Re-peptide bond strengths as indicated by cysteine displacement studies.

The order of addition of the ascorbate acid solution was found to be critical. Addition of ascorbate after the labeling was found to result in stabilization. When the same amount and concentration of ascorbate was added prior to the addition of the rhenium, the RC-160 was not effectively radiolabeled. The results obtained by analytical RP-HPLC were confirmed by TLC studies and by isocratic elutions from C-18 SepPak columns. Even when the amount of ascorbic acid added prior to the addition of the rhenium was reduced to 400 μg the radiolabeling was severely compromised. A side-by-side comparison of the results obtained by RP-HPLC revealed an elution profile indicative of inefficient radiolabeling in the presence of this low amount of ascorbic acid. The RP-HPLC results were confirmed by TLC. In the case of the preparation radiolabeled in the presence of 400 μg of ascorbic acid, further post-addition of addition of ascorbic acid after the labeling did not result in any improvement in the labeling efficiency.

The addition of ascorbate, or ascorbate/sulfite solutions, maximizes the reduction of the peptide RC-160, which is present in excess, without compromising $^{188}$Re-RC-160. The radiolabeling kit can be formulated with an excess of stannous ions and RC-160 to accommodate a variety of labeling situations, such as those that might be expected in field use. In the presence of $^{188}$Re, the RC-160 and stannous ions interact to result in what is believed to be metal-cyclized $^{188}$Re-RC-160. The $^{188}$Re-RC-160 has been demonstrated by RP-HPLC not to be identical with stannous-ion-reduced RC-160, or RC-160 reduced with dithiothreitol. Since $^{188}$Re is produced essentially carrier-free from the W-188/$^{188}$Re generator, excess stannous ions will reduce the RC-160 not complexed to $^{188}$Re. The post-labeling addition of ascorbate maximizes the reduction of excess RC-160, thereby rendering it essentially biologically inactive and unable to compete effectively with $^{188}$Re-RC-160 in vivo for binding to receptors. The net result is a radiolabeled peptide with a very high specific activity.

All of the foregoing are merely illustrative, and other equivalent embodiments are possible and contemplated.

Although the invention has been described with reference to these preferred embodiments, other embodiments can achieve the same results. Variations and modifications of the present invention will be obvious to those skilled in the art and it is intended to cover in the appended claims all such modifications and equivalents. The entire disclosures of all applications, patents, and publications cited above, and of the corresponding application, are hereby incorporated by reference.

What is claimed is:

1. A method of treating rheumatoid arthritis, comprising administration of an effective therapeutic amount of a therapeutic radioisotope-labeled somatostatin-derived peptide analogue by either direct intra-articular injection into a large joint known to be the site of an arthritic inflammation, or injecting the preparation into blood vessels leading to the large joint.

2. The method of claim 1 wherein the therapeutic radioisotope is rhenium in the form of $^{188}$Re or $^{186}$Re.

3. The method of claim 1, wherein the therapeutic radioisotope-labeled somatostatin-derived peptide analogue is in either colloidal or particulate form.

4. The method of claim 1, wherein the therapeutic radioisotope is perrhenate in the form of $^{188}$Re or $^{186}$Re, and is directly labeled to the disulfide bond by a step comprising contacting a solution including the peptide with stannous ions, wherein the amount of stannous ions are sufficient to substantially completely reduce the disulfide bonds of the peptide and the perrhenate, and with the perrhenate, allowing the mixture of peptide, stannous ions and perrhenate to react to form a rhenium-labeled peptide, and recovering the rhenium-labeled peptide.

5. The method of claim 1, wherein the amount of rhenium is between approximately 10 and 500 mCi, and the reaction time is between approximately 1 minute and 4 hours.

* * * * *